United States Patent
Atanackovic et al.

(10) Patent No.: US 8,524,240 B2
(45) Date of Patent: Sep. 3, 2013

(54) DIAGNOSIS AND THERAPY OF HEMATOLOGICAL MALIGNANCIES

(76) Inventors: Djordje Atanackovic, Hamburg (DE); Tim Luetkens, Hamburg (DE)

(*) Notice: Subject to any disclaimer, the term of this patent is extended or adjusted under 35 U.S.C. 154(b) by 240 days.

(21) Appl. No.: 12/911,227

(22) Filed: Oct. 25, 2010

(65) Prior Publication Data

US 2011/0097343 A1  Apr. 28, 2011

Related U.S. Application Data

(60) Provisional application No. 61/254,852, filed on Oct. 26, 2009.

(51) Int. Cl.
| | |
|---|---|
| *A61K 31/00* | (2006.01) |
| *A61K 38/00* | (2006.01) |
| *A61K 39/00* | (2006.01) |
| *A61K 49/00* | (2006.01) |
| *A61B 5/055* | (2006.01) |
| *A01N 61/00* | (2006.01) |
| *C12Q 1/00* | (2006.01) |
| *C12Q 1/68* | (2006.01) |
| *G01N 33/53* | (2006.01) |
| *G01N 33/567* | (2006.01) |
| *G01N 33/574* | (2006.01) |

(52) U.S. Cl.
USPC ......... 424/181.1; 424/9.1; 424/9.2; 424/9.34; 424/178.1; 424/179.1; 424/182.1; 424/183.1; 435/4; 435/6; 435/7.1; 435/7.2; 435/7.21; 435/7.23; 514/1; 514/1.1; 514/19.2; 514/19.3; 514/19.6

(58) Field of Classification Search
None
See application file for complete search history.

(56) References Cited

U.S. PATENT DOCUMENTS

2004/0063101 A1* 4/2004 Scanlan et al. .................... 435/6

FOREIGN PATENT DOCUMENTS

| WO | 2004031354 | 4/2004 |
| WO | 2004043344 | 5/2004 |

OTHER PUBLICATIONS

Dubovsky, et al., "Treatment of chronic lymphocytic leukemia with a hypomethylating agent induces expression of NXF2, an immunogenic cancer testis antigen" ,Clin. Cancer Res.,15:3406-15 (2009).
Dudley, et al., "Cancer regression and autoimmunity in patients after clonal repopulation with antitumor lymphocytes" , Science, 298:850-854 (2002).
Hoffmann and Hauser, "The P-domain or trefoil motif: a role in renewal and pathology of mucous epithelia" , Trends Biochem Sci, 18(7):239-43 (1993).
Kilpinen, et al., "Systematic bioinformatic analysis of expression levels of 17,330 human genes across 9,783 samples from 175 types of healthy and pathological tissues" , Genome Biol., 9(9):R139 (, 2008).
Lee, et al., "Immunomic analysis of human sarcoma" , PNAS, 100(5):2651-6 (2003).
Luetkens, et al., "Cancer-testis antigen FMR1Nb/NY-SAR-35 is expressed on the surface of leukemic blasts with increased proliferative activity" , Cancer Res. Inst. Symposium, New York Oct. 6-8 (abstract book) pg. 83 (2010).
Luetkens, et al., "Expression and immunogenicity of cancer-testis antigens in acute myeloid leukemia" , Eu. J. of Cancer, 7(2):573 (2009).
Luetkens, et al., "Expression of the cancer-testis antigen FMR1NB on the surface of malignant cells" , J of Clinical Oncology, 28(15): e13045 (2010).
Luetkens, et al., "FMR1NB is the first cancer-testis antigen expressed on the surface of malignant cells" , Haematologica, 95 (supp 2): 264, abs. 0629 (2010).
Luetkens, et al., "FMR1NB represents a highly specific surface antigen in patients with acute myeloid leukemia" , Onkologie, 33(suppl 6):273 (2010).
Morgan, et al., "Cancer regression in patients after transfer of genetically engineered lymphocytes" , Science, 314(5796):126-129 (2006).
Nakano, et al., "Proliferative activity of intratumoral CD8(+) T-lymphocytes as a prognostic factor in human renal cell carcinoma: clinicopathologic demonstration of antitumor immunity" , Cancer Res, 61 (13):5132-6 (2001).
Rosenberg, et al. "Cancer regression in patients with metastatic melanoma after the transfer of autologous antitumor lymphocytes" , PNAS, 101:14639-45 (2004).
Simpson, et al., "Cancer/testis antigens, gametogenesis and cancer" , Nat Rev Cancer, 5(8):615-25 (2005).
Soding, et al., "The HHpred interactive server for protein homology detection and structure prediction" , Nucleic Acids Res, 33(Web Server issue):W244-8 (2005).
Wilkins, et al., Protein identification and analysis tools in the ExPASy server. Methods Mol Biol, 112:531-52 (1999).
Zhang, "I-Tasser server for protein 3D structure prediction" , BMC Bioinformatics, 9:40 (2008).

* cited by examiner

*Primary Examiner* — Alana Harris Dent
(74) *Attorney, Agent, or Firm* — Meunier Carlin & Curfman, LLC

(57) ABSTRACT

The present invention relates to the field of diagnosis and therapy of hematological malignancies based on the tumor antigen FMR1NB (also called NY-SAR-35, Cancer/testis antigen 37 or Fragile X mental retardation 1 neighbor protein) and agents specifically targeting this antigen or cells expressing the same, e.g., antibodies. The inventors were able to prove that the molecule is expressed on the cell surface and thus represents a particularly advantageous target in cancer therapy and vaccination. Surprisingly, FMR1NB was found to be associated with hematological malignancies, e.g. acute myeloid leukemia (AML) or chronic myeloid leukemia (CML).

4 Claims, 11 Drawing Sheets

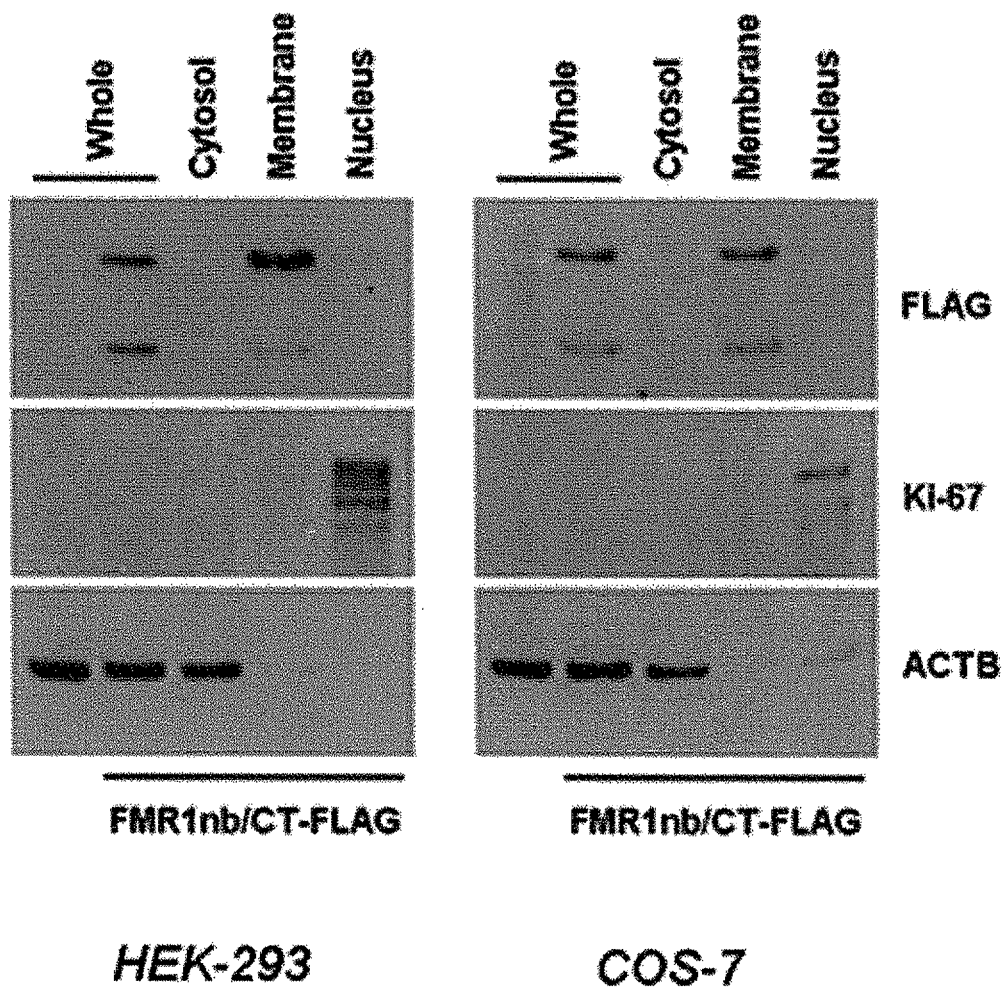

FIG 6

```
         10         20         30         40         50
MSSHRRKAKG RNRRSHRAMR VAHLELATYE LAATESNPES SHPGYEAAMA 60         70         80         90        100
DRPQPGWRES LKMRVSKPFG MLMLSIWILL FVCYYLSYYL CSGSSYFVLA 110        120        130        140        150
NGHILPNSEN AHGQSLEEDS ALEALLNFFF PTTCNLRENQ VAKPCNELQD 160        170        180        190        200
LSESECLRHK CCFSSSGTTS FKCFAPFRDV PKQMMQMFGL GAISLILVCL 210        220        230        240        250
PIYCRSLFWR SEPADDLQRQ DNRVVTGLKK QRRKRKRKSE MLQKAARGRE

255
EHGDE
```

DIAGNOSIS AND THERAPY OF HEMATOLOGICAL MALIGNANCIES

CROSS REFERENCE TO RELATED APPLICATIONS

This application claims benefit of U.S. Provisional Application No. 61/254,852, filed Oct. 26, 2009, which is hereby incorporated herein by reference in its entirety.

FIELD OF THE INVENTION

The invention relates to the field of diagnosis and therapy of hematological malignancies based on the tumor antigen FMR1NB (also called NY-SAR-35, Cancer/testis antigen 37 or Fragile X mental retardation 1 neighbor protein) and agents specifically targeting this antigen or cells expressing the same, e.g., antibodies. The inventors were able to prove that the molecule is expressed on the cell surface and thus represents a particularly advantageous target in cancer therapy and vaccination. Surprisingly, FMR1NB was found to be associated with hematological malignancies, e.g. acute myeloid leukemia (AML) or chronic myeloid leukemia (CML).

BACKGROUND OF THE INVENTION

The notion that the human immune system might be able to detect and eradicate cancer cells has been accepted as well as rejected multiple times in the last century. As early as 1909, Paul Ehrlich assumed that the immune system might be involved in the detection of malignant cells, an idea that was later expanded on by Burnett's and Thomas' hypothesis of "immunosurveillance", stating that the immune system not only observes but is also capable to eliminate these cells. These concepts then became widely unpopular during the 60s and 70s of the last century due to several studies that were unable to show a significant difference in the incidence of tumors between immunocompetent and immunodeficient mice.

Later on, this was again superseded by results now showing an influence of the immune system on the development and the progression of malignant diseases with T cell-mediated immunity playing an important role. Accordingly, it was found that tumor infiltration by T cells and their respective proliferation rate constitute a positive prognostic factor in renal cell [Nakano, O., et al., Cancer Res, 2001, 61(13):5132-6], ovarial, uterine and colon carcinoma, as well as multiple hematologic malignancies, such as Non-Hodgkin lymphoma.

In parallel, knowledge in another domain of tumor immunology, the identification of specific tumor-associated antigens, grew just as rapidly. For a long time, only few tumor antigens were known and thus available for the development of immunotherapeutic agents. This was remedied by an increased scientific effort targeted towards the development of new methods, such as SEREX and T cell epitope mapping, focusing exclusively on the identification of potential immunologic target structures during the last 15 years. The multitude of novel tumor antigens described by these techniques was classified according to their origin, function or expression pattern in comparison to healthy tissues, such as overexpressed antigens or cancer-testis (CT) antigens, with the latter representing an especially promising group of antigens possibly suited for the development of T cell based therapeutic strategies [Simpson, A. J., et al., Nat Rev Cancer, 2005, 5(8): 615-25].

The identification of tumor antigens as target structures for vaccines, antibody therapy or adoptive immunotherapy remains a major goal in the field of tumor immunology. Essential for their use in these settings are a homogenous expression in the tumor, easy accessibility, and highly restricted expression patterns in healthy tissues. CT antigens, a gene family currently containing more than 130 members, are commonly characterized by such specific expression patterns, typically limited to the testis and undetectable in other normal human tissues. A high proportion of CT antigens is located on the X chromosome and these antigens seem to show a particularly tumor-specific expression.

Another distinct property of this group of antigens is their natural immunogenicity, a feature that led to the identification of a large number of members of this gene family via autologous typing. Importantly, CT antigen expression has been described in numerous cancers with widely differing origins and was repeatedly found to be associated with disease progression and loss of differentiation in cancer cells. It has been hypothesized that CT genes might contribute to the appearance of therapy-resistance and, as a consequence, persistence of residual disease in the case of human cancers. Supporting this idea, recent studies have shown that expression of MAGE and GAGE genes in cancer cell lines derived from solid tumors induces a chemotherapy-resistant phenotype in vitro and tumor expression of MAGE-A1 seemed to correlate with clinical responses to taxan-based chemotherapy in gastric cancer patients. Furthermore, it has been hypothesized that expression of CT genes, which are often heterogeneously expressed in tumor tissues by only a certain proportion of cells within the tumor mass, might represent a hallmark of cancer stem cells [Lee, S. Y., et al., Proc Natl Acad Sci USA, 2003, 100(5):2651-6]. These and other results indicate an important biological role of CT antigens for the malignant phenotype. Tumor-specific proteins with a central function in the promotion of the malignancy might represent particularly attractive targets for immunotherapy since (1) the tumor cannot "afford" to down-regulate them under the pressure of immune selection and (2) targeting the cells expressing the given protein might specifically eradicate those cells that guarantee tumor survival and growth.

Unfortunately, despite the remarkable tissue specificity and the distinctive immunogenicity of CT antigens, the development of targeted therapies employing this interesting group of genes has been hampered by the fact that essentially all members of this protein family are limited to the cytosol. Based on this fact, CT antigens have been considered "invisible" to antibody-mediated immune effector mechanisms. Ideally, a CT antigen useful for future immunotherapeutic approaches involving monoclonal antibodies would be naturally located on the malignant cell's surface.

In 2003, several cancer-testis antigens, among them the antigen NY-SAR-35 or, named according to its gene locus FMR1NB, were discovered by Lee et al. of the Ludwig Institute for Cancer Research in a SEREX analysis of sarcoma patients [Lee, S. Y., et al., Proc Natl Acad Sci USA, 2003, 100(5):2651-6; WO 2004/031354]. Following its initial description, this antigen has not been subject to any further investigation either in vitro or in vivo. WO 2004/031354 teaches that NY-SAR-35/FMR1NB represents a newly defined CT antigen expressed exclusively in normal testis, melanoma, sarcoma, lung cancer and breast cancer.

Hematological malignancies are a separate group of cancers, which are derived from cells of a different developmental origin than the cancers previously mentioned. In particular, they originate from blood cells and bone marrow cells as well as immune cells within lymph nodes. Acute myeloid leukemia, AML, is one example of a hematologic malignancy, other diseases from this group comprise chronic myeloid leukemia, acute lymphatic leukemia, chronic lymphatic leukemia, Hodgkin's disease and Non-Hodgkin lymphoma as well as multiple myeloma and myelodysplastic syndrome (MDS). Myeloproliferative diseases are related diseases. While there are treatment options for some of these diseases, further therapeutic approaches are urgently needed.

Acute myeloid leukemia (AML) describes a group of clonal, hemato-logic malignancies that are characterized by the malignant transformation of distinct cell stages from the maturation of hematopoietic progenitor cells. The accumulation of acquired genetic aberrations on one hand leads to a developmental arrest of these pluripotent cells, on the other hand, it promotes uncontrolled proliferation, such as the proliferation caused by mutations in the genes coding for N-Ras and FLT3. AML is the second most common leukemia in adults comprising approximately 90% of acute leukemias with an incidence of 3.6/100.000. Generally, AML can be observed in patients of all ages, but it is characteristically associated with increased age, as indicated by a median age at the time of diagnosis of 65 years. In these patients, mean overall survival is approximately 11 months with a 5-year survival rate of only 20%. Several risk factors contributing to the development of secondary AML have been identified, including chemo- and radiotherapy, as well as a pre-existing myelodysplastic syndrome.

Initial clinical characteristics are usually unspecific symptoms associated with the replacement of the physiological hematopoiesis, such as anemia, impaired coagulation, and frequent infections. At the time of diagnosis of AML, leukopenia might be observed in the peripheral blood of patients, and diagnosis of AML is therefore considered proven only upon the presence of 20-30% of myeloblasts in the bone marrow. Untreated AML will inevitably lead to death within few weeks. The mode of therapy is determined by the FAB (French-American-British) subtype, as well as several prognostic factors such as cytogenetics and the presence of certain molecular markers, but most commonly consists of induction therapy with Daunorubicin or Idarubicin and Cytarabine. Age remains the most important predictor of therapeutic success. Patients younger than 60 years show a 25% higher probability to achieve remission and show a significantly reduced rate of relapses and therapy-related mortality. However, without further therapy, almost all patients will eventually experience relapse following initial remission. Therefore, consolidation treatment (post-remission therapy) is recommended for all patients to extend the duration of the disease-free survival. Consolidation therapy is less uniform than induction therapy and consists of numerous protocols involving different chemotherapeutic options or different modes of stem cell transplantation. However, even by using such an extensive chemotherapeutic regimen, long-term disease-free survival is only achieved in 20-30% of patients.

Another major challenge in the treatment of AML is still posed by the predominantly old and frequently co-morbid patient collective. Only 30% of patients older than 60 years receive conventional induction therapy due to therapy-related mortality in up to 50% of these patients. Although highly selective inclusion criteria were formulated for this group, even patients who receive conventional treatment show vastly reduced remission rates. In addition, subsequent performance of allogeneic stem cell transplantation remains problematic, despite improved non-myeloablative conditioning regimens. Causes for this phenomenon include the lower probability of HLA-matched family donors in older patients and an increased risk for Graft-versus-Host disease.

In the U.S., Gemtuzumab-Ozogamicin, an antibody binding to the lektin CD33 linked to a toxin (WO 2004/043344), has been admitted in consolidation therapy for patients over 60 years of age, where conventional chemotherapy is not indicated. However, approval in Europe was refused due to allegedly insufficient data and an unclear risk-benefit ratio.

To address the severe problems in the current treatment of AML, the development of alternative and more targeted approaches that can be safely applied in such settings is essential. Furthermore, it would be beneficial to develop a means of diagnosis that only requires a blood sample from the patients.

SUMMARY OF THE INVENTION

Methods are therefore provided for treating hematological malignancy in a subject by depleting FMR1NB-positive cells from the subject in vivo or ex vivo. The method can therefore involve administering to the subject a pharmaceutical composition containing an FMR1NB inhibitor. Hematological malignancies include, but are not limited to, acute myeloid leukemia (AML), chronic myeloid leukemia (CML), acute lymphatic leukemia (ALL), chronic lymphatic leukemia (CLL), Hodgkin's disease, Non-Hodgkin lymphoma, multiple myeloma, myelodysplastic syndrome (MDS), and myeloproliferative diseases.

In some embodiments, the FMR1NB inhibitor is an agent the specifically binds FMR1NB. For example, the FMR1NB inhibitor can be an antibody that specifically binds FMR1NB. This agent can be coupled with other active compounds, such as cytotoxic compounds.

In other embodiments, the FMR1NB inhibitor includes autologous or allogeneic FMR1NB-specific T cells. For example, the FMR1NB-specific T cells can be generated by in vivo or ex vivo T cell receptor transduction. Alternatively, the FMR1NB-specific T cells can be generated by in vitro stimulation of T cells.

The disclosed method can also involve administering to the subject a vaccine that depletes FMR1NB-positive cells from the subject. For example, the method can involve administering to the subject a composition that stimulates FMR1NB specific T cells.

In some embodiments, the composition is a FMR1NB protein and/or a nucleic acid encoding a FMR1NB protein. For example, the FMR1NB protein can have an amino acid sequence at least 90% identical to SEQ ID NO:1. Likewise, the FMR1NB protein can be a protein capable of being specifically recognized by an antibody that specifically binds SEQ ID NO:1. In some embodiments, the FMR1NB protein is a fragment of SEQ ID NO:1 having at least one T-cell epitope and/or one B-cell epitope of FMR1NB. Therefore, the FMR1NB protein can have the amino acid sequence SEQ ID NO:1.

A method of diagnosing a hematological malignancy in a subject is also provided. The method can involve detecting FMR1NB expression in and/or on a hematopoietic cell in a sample obtained from the subject. For example, the method can involve detecting FMR1NB protein expression in and/or on the hematopoietic cell. Likewise, the method can involve detecting FMR1NB RNA expression in and/or on the hematopoietic cell. In some embodiments, progression or regression of the malignancy is determined by comparing FMR1NB expression at two or more time points.

A kit for diagnosing a hematological malignancy is also provided. The kit can contain an agent for detecting expression of FMR1NB in and/or on a hematopoietic cell, and an agent for detecting expression of a hematological cell marker.

For example, the hematological cell marker can be a myeloid cell marker. Exemplary myeloid cell markers include CD13, CD33, CD34, and CD45. The agent for detecting expression of FMR1NB or the hematological cell marker can be an antibody that specifically binds FMR1NB or the hematological cell marker.

BRIEF DESCRIPTION OF THE DRAWINGS

FIG. 1B is an immunoblot showing whole lysates and subcellular fractions (Qiagen Qproteome Cell Compartment Kit) from mammalian cell lines that were transfected with mock plasmid or FMR1NB/CT-FLAG, blotted, and stained using the indicated antibodies. ACTB and Ki-67 served as controls for the purity of subcellular fractions.

FIG. 6 shows the amino acid sequence of FMR1NB (SEQ ID NO: 1), the transmembrane regions are underlined. The extracellular domain is indicated in bold, the P type domain in italics (as predicted by UniProtKB). Dotted and dashed lines indicate B cell epitopes extrapolated from hydropathicity and accessibility scores.

DETAILED DESCRIPTION OF THE INVENTION

Figure 1A:
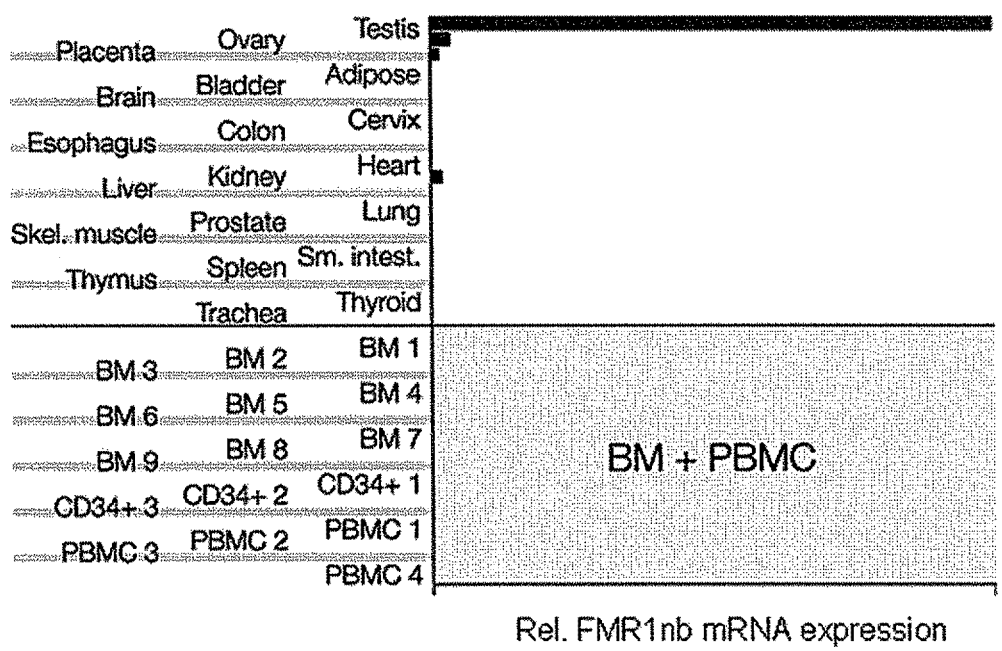
FIG. 1A is a graph showing FMR1NB mRNA expression in healthy tissues assessed by quantitative RT-PCR (Lightcycler, Roche). Values were normalized to the respective sample's GAPDH expression level. Bars indicate FMR1NB expression levels relative to testis.

In light of the state of the art, the inventors were faced with the problem of developing a novel and advantageous target for therapy and diagnostic of a hematological malignancy, and a therapeutic approach based thereon.

Surprisingly, in a comprehensive analysis of myeloid malignancies performed by the inventors, a highly restricted expression of the FMR1NB antigen was detected in a significant number of AML and CML cell lines as well as in samples from patients with hematological malignancies. In contrast, FMR1NB was not detected in any healthy tissues, apart from testis, which is in line with comprehensive public gene expression data of healthy tissue arrays [Kilpinen, S., et al., Genome Biol, 2008, 9(9):R139]. These findings demonstrate the typical expression pattern of a cancer-testis antigen.

The present invention therefore provides the use of an agent capable of specifically targeting FMR1NB or cells expressing the same for the preparation of a pharmaceutical composition for treatment of a hematological malignancy.

The invention further provides a method of treatment for a hematological malignancy, wherein an agent capable of specifically targeting FMR1NB or cells expressing the same, in particular an agent capable of specifically binding to FMR1NB is administered to a patient suffering from a hematological malignancy.

The invention provides the use of an agent capable of specifically binding to FMR1NB for the preparation of a pharmaceutical composition for treatment of a hematological malignancy or of a diagnostic for diagnosing a hematological malignancy.

FMR1NB is the tumor antigen the inventors found to be expressed in hematological malignancies. It preferably comprises SEQ ID NO: 1 or consists thereof.

The agent may be a small molecule specifically binding to FMR1NB or a natural ligand of FMR1NB, which can, e.g., be identified by binding assays such as the yeast two hybrid system. In one embodiment, the agent comprises an antibody, preferably, a monoclonal and/or recombinant antibody. In particular, for therapeutic approaches, the antibody may be a chimeric, human or humanized antibody, which prevents or reduces immunogenicity. Preferably, the antibody is a recombinant monoclonal human or humanized antibody. The antibody may also be a single chain antibody, an antigen binding fragment of an antibody, e.g., a Fab of F(ab)$_2$ fragment or a polyclonal antibody.

The agent, e.g., the antibody, may be coupled to an active compound, e.g., a cytotoxic compound, an enzyme, such as an enzyme that converts a non-toxic compound to a cytotoxic compound, a radioisotope or a detectable, e.g., fluorescent, label. Examples of active compounds suitable for therapeutic purposes are known from the state of the art, e.g., calicheamin, esperamin, methotrexate, doxorubicin, melphalan, chlorambucil, ARA-C, vindesine, mitomycin C, cisplatin, etopside, bleomycin and fluorouracil. Radioisotopes include: $^{225}Ac$, $^{211}At$, $^{212}Bi$, $^{213}Bi$, $^{186}Rh$, $^{188}Rh$, $^{177}Lu$, $^{90}Y$, $^{131}I$, $^{67}Cu$, $^{125}I$, $^{123}I$, $^{77}Br$, $^{153}Sm$, $^{166}Bo$, $^{64}Cu$, $^{212}Pb$, $^{224}Ra$ and $^{223}Ra$.

The agent may target cells expressing FMR1NB. The agent may comprise FMR1NB-specific T cells, which can be autologous or allogeneic FMR1NB-specific T cells. The FMR1NB-specific T cells may be generated in vivo, e.g., by vaccination of the patient or a different human individual sharing at least one, preferably, all HLA types. Such T cells can be isolated and further stimulated/propagated in vitro. FMR1NB-specific T cells may also be generated ex vivo, e.g., by transduction of T cells with a FMR1NB-specific T cell receptor [Morgan, R. A., et al. Science, 2006, 314(5796):126-129] and/or in vitro induction and/or expansion of FMR1NB-specific T cells, which may, e.g., be isolated from the patient. A FMR1NB protein (or peptide) or a nucleic acid (RNA or DNA) encoding the same, as defined below, may be used for immunization and/or in vitro stimulation, e.g., a protein comprising a fragment of FMR1NB comprising at least one T cell epitope thereof, or a protein having at least 90% amino acid identity to SEQ ID NO:1. The selection of T cell epitopes of FMR1NB according to the HLA type of the patient is well known to the skilled person. T cell epitopes can, e.g., be predicted by software based on the HLA type of the patient. Stimulation of T cells in vivo with appropriate peptides is also routine in the art. Preferably, CD4 and CD8 positive T cells are generated (together or separately) and used for adoptive transfer. The present invention thus teaches the adoptive transfer of FMR1NB-specific T cells (CD4 positive T cells and/or CD8 positive T cells) to a patient suffering from a hematological malignancy. Similar protocols targeting other tumor antigens have been successfully used in the art and can be adapted to targeting FMR1NB [Dudley, M. E. et al. Science, 2002, 298:850-854; Rosenberg, S. E. et al. Proc Natl Acad Sci USA, 2004, 101:14639-45].

In one embodiment of the invention, the pharmaceutical composition is formulated for reduction and/or depletion of FMR1NB-positive cells from the patient in vivo. The pharmaceutical composition may be formulated for infusion. Methods of administration, treatment regimens and dosing may be selected by the skilled person as known for similar agents from the state of the art, e.g., if the agent comprises an antibody, as known from Gemtuzumab, in particular Gemtuzumab-Ozogamicin (WO 2004/043344). The pharmaceutical formulation may also be administered in combination with Gemtuzumab-Ozogamicin, i.e., simultaneously, before and/or after administration of Gemtuzumab-Ozogamicin. The pharmaceutical formulation may also be used in combination with other treatment regimens and medicaments. The pharmaceutical composition may be employed in induction therapy and/or consolidation therapy and/or maintenance therapy.

In another embodiment of the invention, the pharmaceutical composition is formulated for reduction and/or depletion of FMR1NB-positive cells from the blood of the patient ex vivo. For example, the agent capable of binding to FMR1NB, such as an antibody, may be linked to a solid carrier under conditions suitable for binding to the antigen on the patient's cells, and blood from the patient may be brought into contact with the carrier, to be re-infused into the patient after separation from the carrier and depletion of the cells. Of course, other options known in the state of the art can be adapted for depletion of FMR1NB positive cells.

The invention further provides use of a composition comprising a FMR1NB protein and/or a nucleic acid encoding a FMR1NB protein for the preparation of a prophylactic or therapeutic vaccine for treatment of a hematological malignancy or for in vitro stimulation of allogeneic or autologous T-cells.

FMR1NB specific T cells stimulated and propagated in this way may be used for adoptive transfer into a patient suffering from a hematological malignancy. The skilled person will be easily aware of the HLA requirements depending on the patient and make appropriate accommodations. Such T cells may also be used for research purposes or for cloning an FMR1NB specific T cell receptor (TCR).

In the context of the invention, a FMR1NB protein comprises a sequence having at least 90% amino acid identity to a protein of SEQ ID NO: 1, or a fragment thereof comprising at least one T-cell epitope and/or at least one B-cell epitope of FMR1NB. The FMR1NB protein, in particular the sequence having at least 90% amino acid identity to a protein of SEQ ID NO: 1, is preferably capable of being specifically recognized by an antibody against FMR1NB of SEQ ID NO:1, e.g., a polyclonal antibody preparation commercially available from Abnova, Taiwan. Preferably, a FMR1NB protein comprises more than one T-cell epitope, e.g., one or more CD4 T cell epitopes and/or one or more CD8 T cell epitopes. For the purposes of vaccination, it is preferred to use the complete FMR1NB protein (or nucleic acids encoding it) or proteins or peptides comprising a selection of T cell epitopes appropriate for the most common HLA types.

Epitopes which can be used are disclosed herein, however, the skilled person will be able to identify further epitopes which may be more appropriate, e.g., depending on the patient.

Preferably, the FMR1NB protein comprises a sequence having at least 80%, at least 90%, least 95% or at least 98% or at least 99% amino acid identity to a protein of SEQ ID NO: 1. More preferably, the FMR1NB protein comprises the sequence of the mature FMR1NB protein, a natural allele thereof, or a sequence of at least one T-cell epitope and/or B-cell epitope. Most preferably, the FMR1NB protein comprises a sequence selected from the group comprising SEQ ID NO:1. In one embodiment, the FMR1NB protein comprises a sequence having at least 80%, at least 90%, at least 95%, at least 98% or at least 99% amino acid identity to a protein of SEQ ID NO: 1, wherein the protein comprises the sequence of one or more T cell epitope and/or B cell epitope disclosed herein. It is known that one or more amino acid exchanges, deletions or introductions often do not change the structure, immunological properties and/or binding characteristics of a protein, in particular with conservative amino acid substitutions.

Without intending to be bound by the theory, performing comparative structural analyses of the initially described mRNA sequence, it was found that the FMR1NB protein of SEQ ID NO: 1, consists of 255 amino acids (aa), forms two transmembrane domains and a highly conserved extracellular p-type motif commonly observed in intestinal trefoil proteins, a family of protective factors secreted by mucosa tissues [Hoffmann, W. and F. Hauser, Trends Biochem Sci, 1993, 18(7):239-43]. B-cell epitopes can be expected to be situated in the extracellular domain of FMR1NB.

Novel structural and functional prediction software employing the hidden markov model showed a significant functional homology with human arginase 1, as illustrated by an OH-binding site within its trefoil domain [Zhang, Y., BMC Bioinformatics, 2008, 9:40; Soding, J., et al., Nucleic Acids Res, 2005, 33:W244-8].

In the context of the invention, FMR1NB proteins include fusion proteins of FMR1NB proteins or fragments, e.g., fragments thereof comprising a B-cell epitope and/or T-cell epitope. Examples are fusion proteins with a His-Tag, GST-Tag, FLAG-Tag, GFP-tag or with components intended to enhance the immune response. Examples of fusion proteins are disclosed herein.

TABLE 1

T cell epitopes for common HLA types,
predicted with www.syfpeithi.de.

| HLA class I (9mers) | | HLA class II (15mers) | |
|---|---|---|---|
| SEQ ID NO: 13-52 | SEQ ID NO: 53-92 | SEQ ID NO: 93-132 | |
| Pos | Pos | | Pos |
| HLA-A1 | HLA-B7 | HLA-DR1 | |
| NPESSHPGY | 37 KPCNELQDL | 143 MMQMFGLGAISLILV | 184 |
| LFVCYYLSY | 80 HPGYEAAMA | 42 PKQMMQMFGLGAISL | 181 |
| IWILLFVCY | 76 RVSKPFGML | 64 SSYFVLANGHILPNS | 94 |
| LSESECLRH | 151 LPIYCRSLF | 200 SLFWRSEPADDLQRQ | 206 |
| VAHLELATY | 21 AMRVAHLEL | 18 HPGYEAAMADRPQPG | 42 |
| WILLFVCYY | 77 VPKQMMQMF | 180 SLKMRVSKPFGMLML | 60 |
| YYLCSGSSY | 88 AISLILVCL | 192 KMRVSKPFGMLMLSI | 62 |
| LILVCLPIY | 195 EDSALEALL | 118 GSSYFVLANGHILPN | 93 |
| ATESNPESS | 23 QVAKPCNEL | 140 KCCFSSSGTTSFKCF | 160 |
| FVCYYLSYY | 81 WRSEPADDL | 209 FAPFRDVPKQMMQMF | 174 |
| HLA-A2 | HLA-B8 | HLA-DR3 | |
| AISLILVCL | 192 KRKRKSEML | 234 DSALEALLNFFFPTT | 119 |
| MLMLSIWIL | 71 SLKMRVSKP | 60 LVCLPIYCRSLFWRS | 197 |
| HLELATYEL | 23 KAKGRNRRS | 7 GMLMLSIWILLFVCY | 70 |
| ILLFVCYYL | 78 VPKQMMQMF | 180 GQSLEEDSALEALLN | 113 |
| AMRVAHLEL | 18 CLRHKCCFS | 156 PFGMLMLSIWILLFV | 68 |
| SLILVCLPI | 194 RRKRKRKSE | 232 NGHILPNSENAHGQS | 101 |
| CLPIYCRSL | 199 RRKAKGRNR | 5 SIWILLFVCYYLSYY | 75 |
| LMLSIWILL | 72 HRAMRVAHL | 16 AMRVAHLELATYELA | 18 |
| GLGAISLIL | 189 SHRRKAKGR | 3 RESLKMRVSKPFGML | 58 |
| GMLMLSIWI | 70 HLELATYEL | 23 FGMLMLSIWILLFVC | 69 |
| HLA-A3 | HLA-B15 | HLA-DR4 | |
| NLRENQVAK | 135 MLSIWILLF | 73 LATYELAATESNPES | 26 |
| KQRRKRKRK | 230 YLCSGSSYF | 89 GSSYFVLANGHILPN | 93 |
| KRKSEMLQK | 236 FVCYYLSYY | 81 SSYFVLANGHILPNS | 94 |
| RVAHLELAT | 20 ALEALLNFF | 121 LLNFFFPTTCNLREN | 125 |
| ESLKMRVSK | 59 WILLFVCYY | 77 FKCFAPFRDVPKQMM | 171 |
| FVCYYLSYY | 81 LILVCLPIY | 195 FAPFRDVPKQMMQMF | 174 |
| YLCSGSSYF | 89 SLKMRVSKP | 60 SLFWRSEPADDLQRQ | 206 |
| ALEALLNFF | 121 NLRENQVAK | 135 HRAMRVAHLELATYE | 16 |
| SLILVCLPI | 194 SLILVCLPI | 194 VAHLELATYELAATE | 21 |
| VVTGLKKQR | 224 VAHLELATY | 21 PFGMLMLSIWILLFV | 68 |

TABLE 1-continued

T cell epitopes for common HLA types,
predicted with www.syfpeithi.de.

| HLA class I (9mers) | | HLA class II (15mers) | |
|---|---|---|---|
| SEQ ID NO: 13-52 | SEQ ID NO: 53-92 | SEQ ID NO: 93-132 | |
| Pos | Pos | | Pos |
| HLA-A24 | HLA-B44 | HLA-DR7 | |
| YFVLANGHI | 96 EEDSALEAL | 117 LSYYLCSGSSYFVLA | 86 |
| FFFPTTCNL | 128 SENAHGQSL | 108 KCCFSSSGTTSFKCF | 160 |
| PFGMLMLSI | 68 LEALLNFFF | 122 LLNFFFPTTCNLREN | 125 |
| MFGLGAISL | 187 AISLILVCL | 192 LATYELAATESNPES | 26 |
| LMLSIWILL | 72 MLSIWILLF | 73 TYELAATESNPESSH | 28 |
| FGLGAISLI | 188 IWILLFVCY | 76 QPGWRESLKMRVSKP | 54 |
| QSLEEDSAL | 114 FFFPTTCNL | 128 LLFVCYYLSYYLCSG | 79 |
| SALEALLNF | 120 MLMLSIWIL | 71 SYYLCSGSSYFVLAN | 87 |
| LPIYCRSLF | 200 ALEALLNFF | 121 GSSYFVLANGHILPN | 93 |
| HRAMRVAHL | 16 SECLRHKCC | 154 SSYFVLANGHILPNS | 94 |

The vaccines may comprise at least one FMR1NB protein and/or at least one nucleic acid encoding a FMR1NB protein, as defined above. Methods suitable for vaccination with nucleic acids, e.g., DNA or RNA are known in the state of the art. For example, viral vectors, such as adenoviral vectors or liposomes can be used for delivery of the effective agent for vaccination. A preferred nucleic acid encodes at least one FMR1NB protein as described above. In one embodiment, the nucleic acid comprises a sequence of SEQ ID NO: 2 or a fragment thereof encoding a B cell epitope and/or a T cell epitope. Due to the degeneracy of the genetic code, different codons may be used to encode the protein of SEQ ID NO: 1, e.g., accommodations may be made for introduction of a higher GC content, which is known to enhance immunogenecity. Often, more than one, e.g., two of three doses of a vaccine of the invention are administered to boost immunogenicity.

The hematological malignancy can be leukemia or lymphoma. In the context of the invention, the hematological malignancy may be acute myeloid leukemia (AML), chronic myeloid leukemia (CML), acute lymphatic leukemia (ALL), chronic lymphatic leukemia (CLL), Hodgkin's disease, Non-Hodgkin lymphoma, multiple myeloma, myelodysplastic syndrome (MDS) or myeloproliferative diseases. Preferably, the hematological malignancy is a myeloid malignancy. Usually, hematological malignancies do not form solid tumors.

A composition suitable for vaccination may further comprise an adjuvant and/or other pharmacologically acceptable excipients.

The present invention further provides a method of diagnosing a hematological malignancy in a subject, comprising steps wherein the expression of FMR1NB, in particular having SEQ ID NO:1, in and/or on a hematopoietic cell is detected in a sample obtained from the patient.

The sample may be a blood sample, a bone marrow sample, a sample of lymphoid tissue, or a sample from other tissues containing hematopoietic cells. In particular, the expression of FMR1NB in and/or on a myeloid cell is detected. The sample may be contacted with an agent capable of binding to FMR1NB protein, e.g., an antibody, or a nucleic acid capable of hybridizing to FMR1NB RNA or cDNA. The expression may be detected on the protein level, e.g., by flow cytometric analysis (e.g., FACS), cytospin or an immunoblot, such as a Western blot or a dot blot. As the inventors have shown membrane expression of the antigen on hematological cancer cells, intracellular staining may be used, it is however not required.

The expression may also be detected on the RNA level, e.g., by amplification and/or hybridization techniques, e.g., Northern Blot, array technology and/or RT-PCR. Real time PCR may be employed, e.g., a light Cycler™ (Roche). Examples of suitable primers or probes and conditions for detecting expression are disclosed herein or in Lee at al [Lee, S. Y., et al., Proc Natl Acad Sci USA, 2003, 100(5):2651-6], which is included herein by reference in its entirety, but other suitable primers or probes capable of hybridizing to the FMR1NB nucleic acid (SEQ ID NO: 2) under suitable conditions can be prepared by one of skill in the art.

Detection of FMR1NB in and/or on a hematopoietic cell indicates that the patient suffers from a hematological malignancy. In one embodiment, FMR1NB is expressed by more than 10%, more than 20%, more than 30%, more than 50% or more than 80% of the hematological, in particular, myeloid cells of the patient.

The method of the invention of diagnosing a hematological malignancy can be employed for determining progression or regression of the malignancy in a subject, wherein the expression of FMR1NB in and/or on a hematopoietic cell in samples obtained from the patient at two or more time points, e.g., before, during and after treatment, is compared. A decreasing expression of FMR1NB on hematological, in particular myeloid, cells indicates regression of the malignancy and success of treatment.

The present invention further provides a kit for diagnosing a hematological malignancy, comprising (a) an agent for detecting expression of FMR1NB, in particular FMR1NB of SEQ ID NO:1 in and/or on a hematopoietic cell, and at least one (b) an agent for detecting expression of a hematological cell marker.

Preferably, the hematological cell marker is a myeloid cell marker, e.g., CD13, CD33, CD34 and CD45. The kit can also comprise two, three, four or more agents for detecting expression of a the hematological cell marker, as it has been found that cancer cells of some patients may or may not express specific hematological markers.

Preferably, if expression is to be detected on the protein level, the agents are antibodies. It is advantageous if both antibodies are labeled with different labels, or if the antibodies belong to different isotypes or are derived from different species to enable simultaneous staining and detection. The agents may also be nucleic acids if expression of FMR1NB is to be detected on the RNA level.

In the context of the invention, the patient preferably is a human subject, but the patient may also be, e.g., a mouse, a pig, a cat, a dog, a horse, cattle or an ape.

These data provided by the inventors indicate that FMR1NB is selectively upregulated in myeloid leukemias and other hematologic malignancies, and that it represents a surface molecule, a transmembrane protein which comprises containing a continuous extracellular domain spanning approximately 90 aa.

Figure 1C:
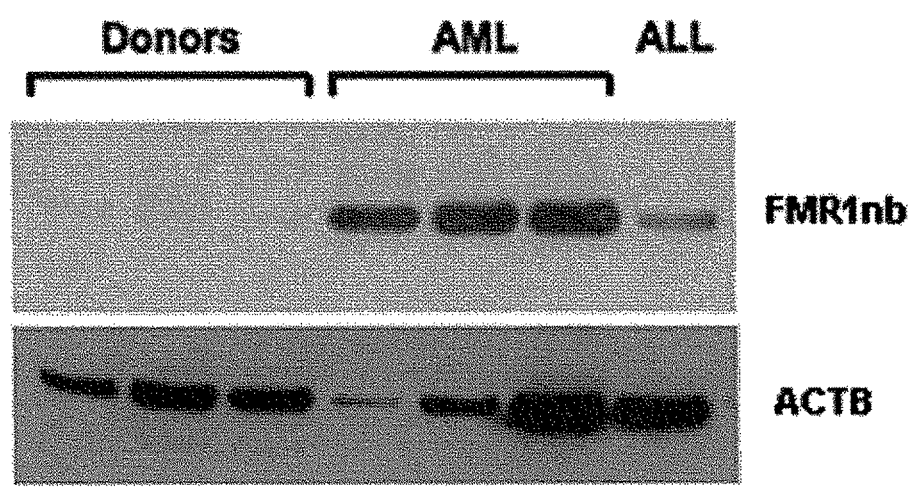
FIG. 1C is an immunoblot showing whole lysates of representative peripheral blood samples from three healthy donors and patients with AML or acute lymphocytic leukemia blotted and stained using anti-FMR1NB antibody (Abnova, Taiwan).

The inventors have confirmed the highly restricted expression pattern of FMR1NB in healthy tissues as demonstrated by quantitative RT-PCR of healthy tissues (FIG. 1A). Protein expression of FMR1NB in multiple hematologic malignancies was investigated by the inventors. In order to assess protein expression, the molecular weight of FMR1NB protein for subsequent western blot assays was first established. A carboxy-terminal FLAG-construct FMR1NB/CT-FLAG of the FMR1NB open-reading frame amplified from testis RNA was generated. The construct was then cloned into pcDNA3.1 and sequencing confirmed coverage and identity of the FMR1NB insert with the respective consensus coding sequence. Using a monoclonal anti-FLAG antibody, two distinct bands were observed in lysates from FMR1NB/CT-FLAG transfected HEK-293 and COS-7 cells at approximately 32 kDa and 18 kDa, the latter corresponding to the calculated molecular weight of native FMR1NB protein (FIG. 1B). Focusing on these bands using commercially available polyclonal antibodies raised against full-length FMR1NB protein, distinct 32 kDa bands were observed in multiple AML cell lines as well as in peripheral blood samples from AML patients. Importantly, the respective band was absent from blood samples from healthy donors (FIG. 1C). Performing blocking experiments using recombinant protein (Abnova, Taiwan), this band was confirmed to be specific for FMR1NB (data not shown).

Figure 1D:
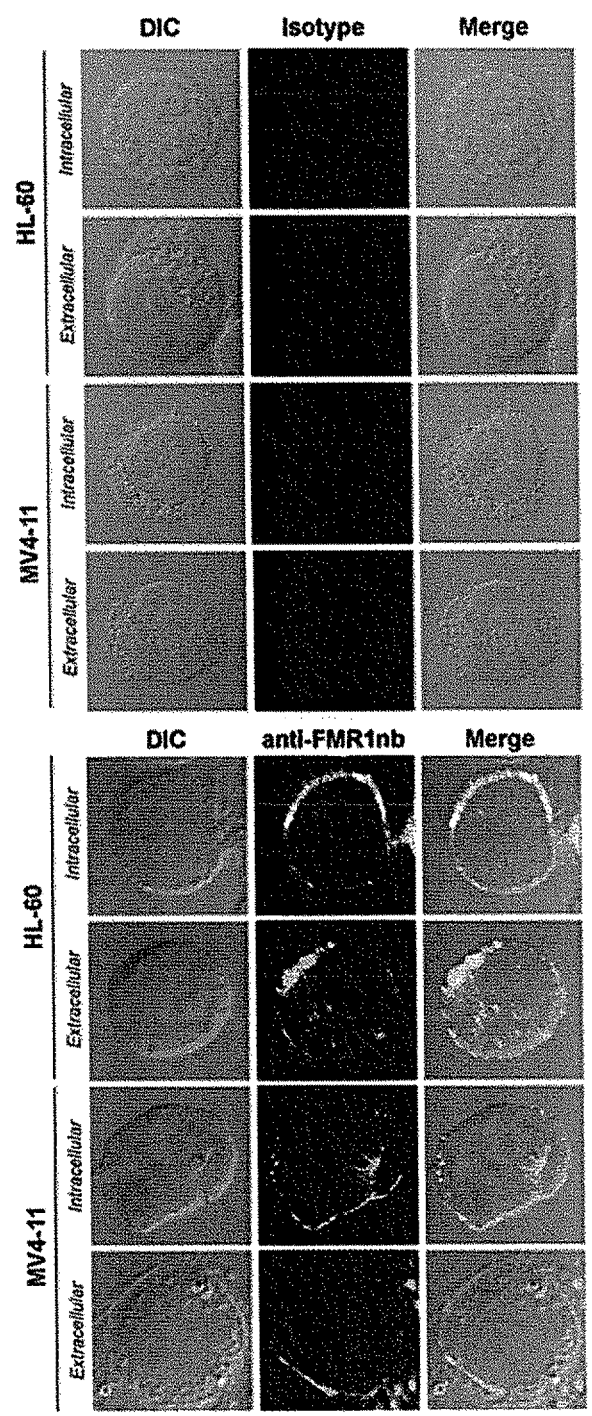
FIG. 1D are DIC and fluorescence images were obtained using confocal microscopy (Leica TCS SPE) of intact or permeabilized AML cell lines stained using mouse anti-FMR1NB and anti-mouse IgG FITC.
Figure 2A:
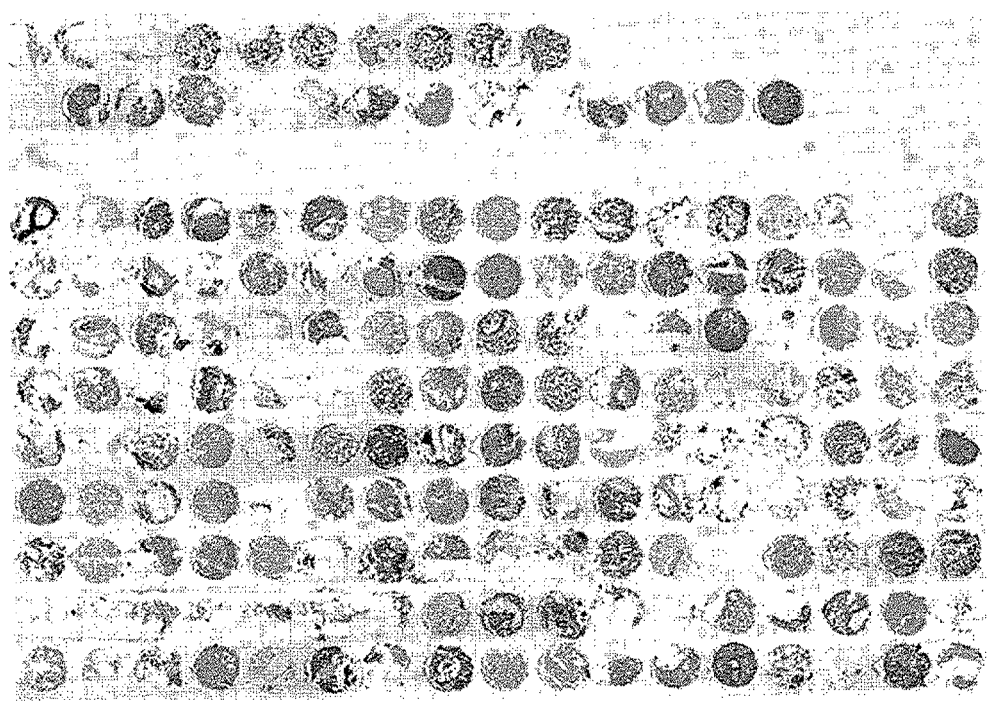
FIG. 2A contains images obtained using an automated Mirax Scan system (Carl Zeiss) showing single cell layers of bone marrow biopsies from 153 newly diagnosed AML patients, spotted on microscope slides, and stained by immunohistochemistry using anti-FMR1NB antibody. A resized scan of the whole array slide is shown.
Figure 2B:
FIG. 2B contains images representing 1:1 crops of individual spots from FIG. 2A.

Immunofluorescence stainings of permeabilized and intact AML cell lines were performed using polyclonal anti-FMR1NB antibody (Abnova, Taiwan). The inventors observed a specific staining following both procedures, showing a localization of FMR1NB at the plasma membrane by confocal microscopy (FIG. 1D). The inventors next performed an immunohistochemistry staining of a tissue microarray containing 153 bone marrow biopsies from newly diagnosed patients with AML (FIG. 2A). The majority of the samples showed a frequent expression of FMR1NB, and the results on the cellular level again indicated a membrane expression of the protein (FIG. 2B).

Figure 3A:
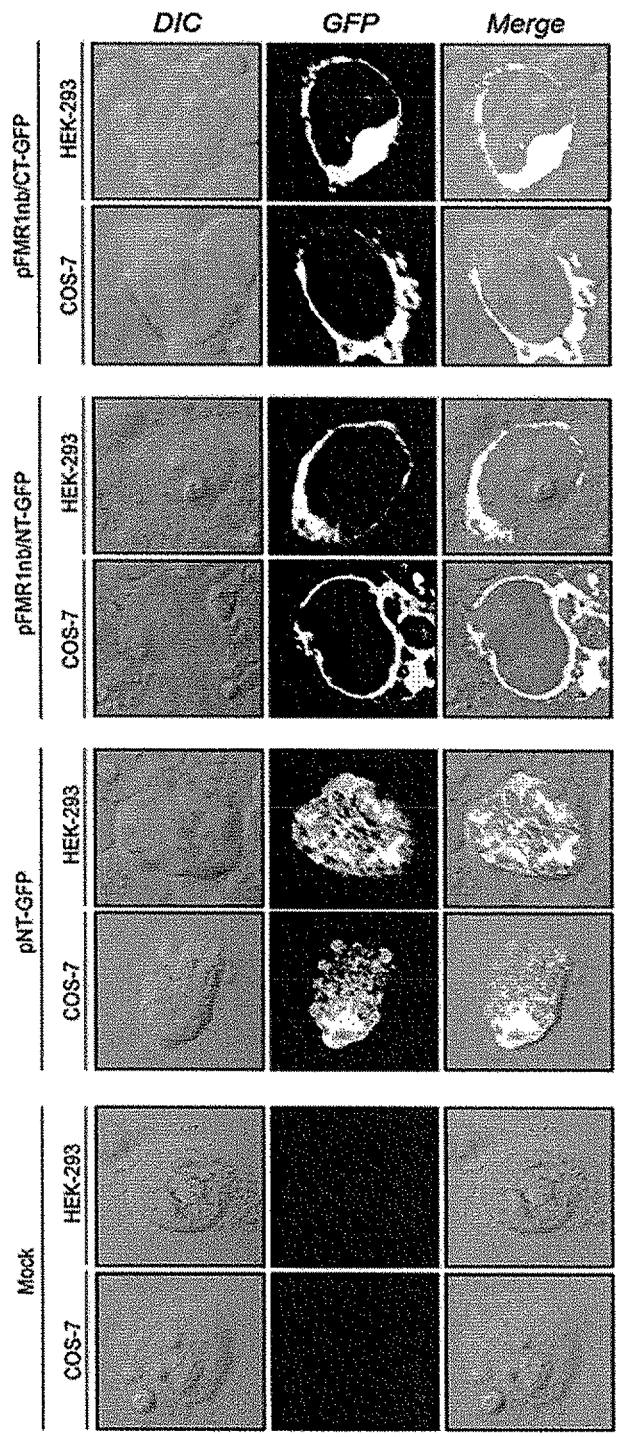
FIG. 3A are DIC and fluorescence images obtained using confocal microscopy of HEK-293 and COS-7 cells transfected with FMR1NB/CT-GFP, FMR1NB/NT-GFP or GFP alone.
Figure 3B:
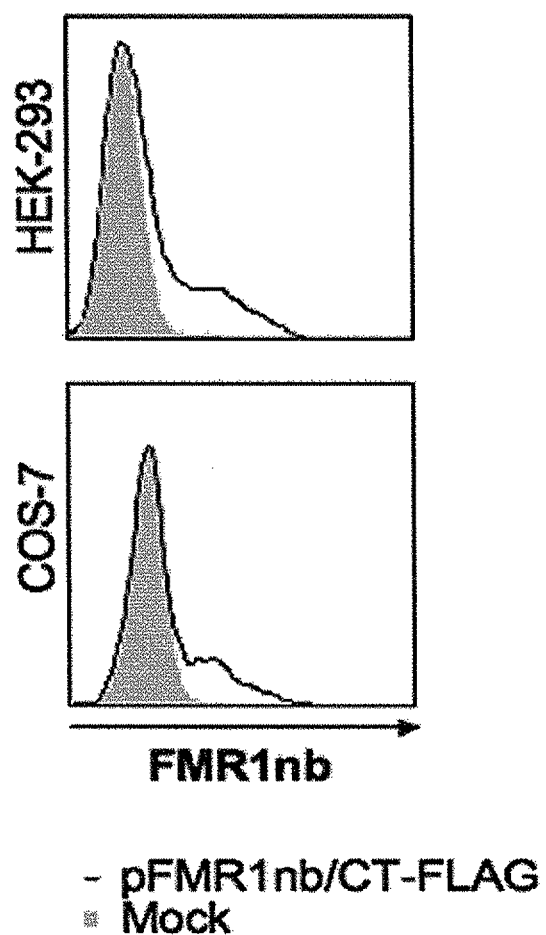
FIG. 3B are flow cytometry graphs depicting FMR1NB expression in HEK-293 (top graph) and COS-7 (bottom graph) cells transfected with FMR1NB/CT-FLAG (solid line) or mock plasmid (shaded area), stained using anti-FMR1nNB antibody and anti-mouse IgG FITC, were analyzed by flow cytometry (BD Facscalibur).

In order to confirm these findings using an antibody-independent approach, several FMR1NB expression constructs were generated. The nucleotide sequences coding for GFP or a FLAG tag were coupled to the carboxy- or the amino-terminus of the open reading frame of FMR1NB and cloned into pcDNA3.1. Overlays of confocal GFP and differential interference contrast (DIC) images of HEK-293 and COS-7 cells transfected with the FMR1NB/GFP constructs or GFP alone demonstrate a predominant membraneous localization of FMR1NB (FIG. 3A). This was further confirmed performing FACS analyses of both mammalian cell lines transfected with FMR1NB/CT-FLAG following extracellular staining with anti-FMR1NB-antibody (FIG. 3B). Separation of subcellular fractions using a commercial fractionation kit and subsequent immunoblot using anti-FLAG antibody demonstrates the presence of both previously determined FMR1NB specific bands in the membrane fraction, but not the cytosolic of nuclear fraction (FIG. 1B). Ki-67 and ACTB controls demonstrate purity of the fractions. As carboxy- and aminoterminal FLAG-constructs resulted in the same band pattern, the inventors propose that posttranslational modification does not include cleavage of the original FMR1NB protein.

Figure 4A:
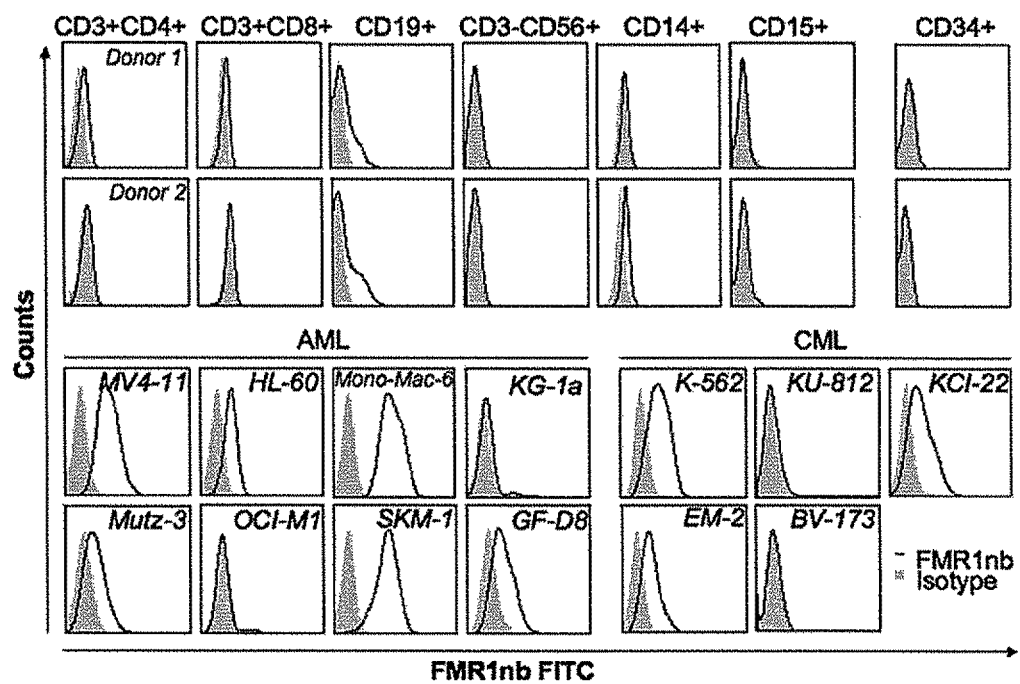
FIG. 4A are flow cytometry graphs depicting FMR1NB expression in AML and chronic myeloid leukemia cell lines, as well as peripheral blood samples from 10 healthy donors that were stained using anti-FMR1NB, anti-mouse IgG FITC, and PE- or APC-conjugated population-specific antibodies. Results are shown for two representative donors.
Figure 4B:
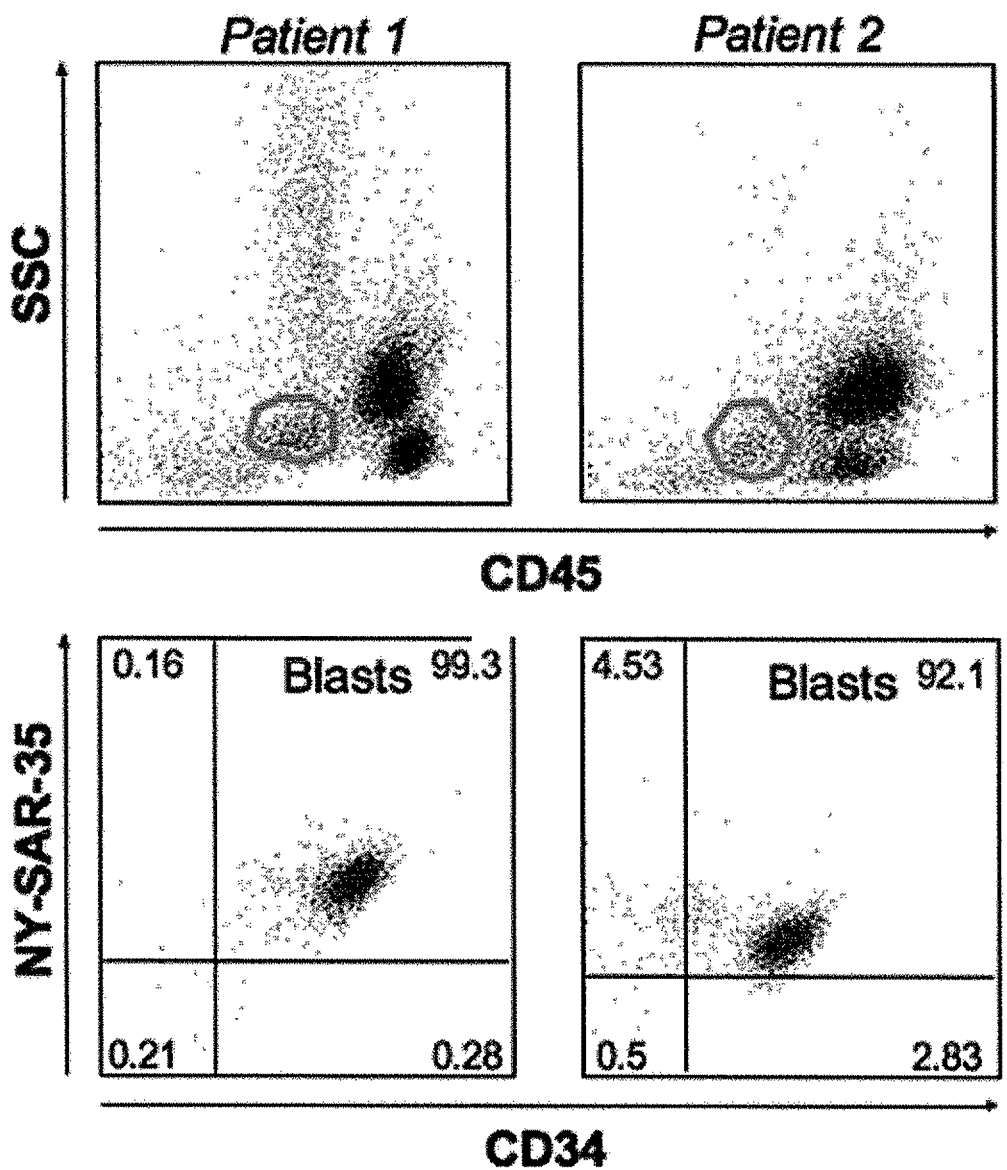
FIG. 4B are flow cytometry plots showing FMR1NB expression in peripheral blood samples from 20 patients with AML analyzed by flow cytometry after staining with anti-CD45, anti-FMR1NB, and anti-mouse IgG FITC. Results are shown for two representative samples.
Figure 5:
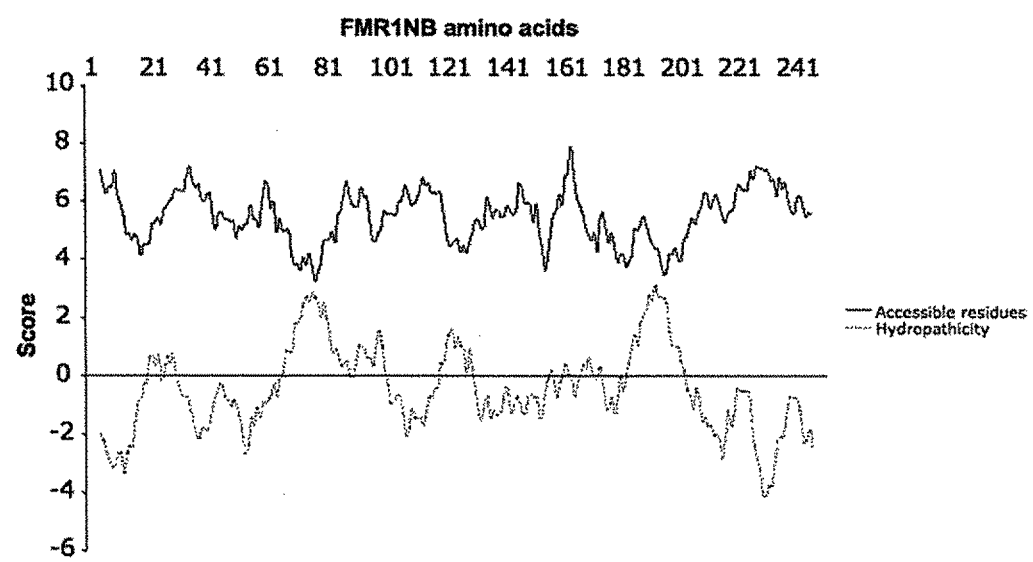
FIG. 5 is a graph showing the scores of the percentage of accessible residues (solid line) and Kyte-Doolittle hydropathicity (dotted line) of FMR1NB protein [Wilkins, M. R., et al., Methods Mol Biol, 1999, 112:531-52]. Hydrophobic peaks between residues 69 and 92, as well as 185 and 207, are in line with predicted transmembrane domains in these segments.

Combining the findings of a highly restricted expression of FMR1NB in myeloid leukemia as well as the ability to stain the extracellular domain of FMR1NB with the polyclonal antibody, the possibility of analyzing FMR1NB expression on leukemia cell lines and primary cells from patients and healthy donors by flow cytometry was investigated. Staining of donor cell populations using anti-FMR1NB indicated that surface expression of this protein is absent from healthy hematopoietic cells (FIG. 4A). In contrast, significant levels of FMR1NB were observed on the surface of the majority of cell lines derived from patients with acute or chronic myeloid leukemia cells (FIG. 4A). This was also confirmed in peripheral blood samples from a group of 20 AML patients after gating on leukemic blasts. In all of these patients, homogenous surface expression of FMR1NB was found on the leukemic blasts (FIG. 4B).

These findings show that FMR1NB may be the CT antigen most frequently expressed by AML and other hematological malignancies. Even more importantly, the inventors proved that FMR1NB represents the first of all chromosome X cancer-testis antigens expressed on the surface of tumor cells. The invention opens the route for new applications for FMR1NB, for example as a target for monoclonal antibodies in diagnosis and therapy. Such tumor-specific antibodies can be used for diagnostic purposes or in novel and promising modes of therapy for patients with AML, CML or other hematological malignancies.

EXAMPLES

Example 1

Peripheral Blood Samples and AML Cell Lines

Mononuclear cells (MNC) were isolated from PBL (peripheral blood leukocyte) samples by density gradient centrifugation and were washed twice with phosphate-buffered saline (PBS). MNC and cells from cell lines were lysed using RLT Buffer (Qiagen, Hilden, Germany) or protein lysis buffer containing Protease Inhibitor Cocktail (Sigma-Aldrich, St. Louis, Mo., USA) and were stored at −80° C. until needed. For localization experiments, subcellular fractions were obtained from whole cell samples using the Qiagen Cell Compartment kit according to the provided manual. Cell lines were obtained from DSMZ (Braunschweig, Germany) and were maintained in RPMI 1640 with 10% fetal calf serum (FCS).

Quantitative Reverse Transcription PCR (RT-PCR)

Extraction of total RNA and reverse transcription from AML cell lines and PBL samples were performed using the RNeasy Mini Kit (Qiagen, Hilden, Germany) and AMV reverse transcriptase (Promega, Madison, Wis.). Reverse transcription was run at 42° C. for 45 min with heat inactivation of the enzyme at 95° C. for 5 min. A master mix of the following components was prepared at the indicated final concentrations: 4.0 mM MgCl2, 400 nM forward and reverse primers (forward primer: ACCTGTGCTCCGGGTCCTCA (SEQ ID NO:3); reverse primer: GGCTGATCGCACCAAGCCCA (SEQ ID NO:4); product length: 318 [340-657]), 200 nM dNTP (Invitrogen, Karlsruhe Germany), 1% DMF, BSA at 250 µg/ml, SYBR Green I (Sigma, St. Louis, Mo.) diluted 1:20,000, and I Unit FastStart Taq polymerase (Roche Diagnostics, Branchburg, N.J.) in a total volume of 20 µl. After an initial denaturation at 95° C. for 10 minutes, PCR reactions were cycled 40 times. Fluorescence intensity was measured at the end of each elongation phase. A melting curve analysis was carried out immediately after amplification. A standard curve prepared of the PCR product cloned into a pCR2.1 vector using the TA cloning kit (Invitrogen, Carlsbad, Calif., USA) was prepared to determine the concentration of target transcripts in cDNA samples.

Western Blot

Lysates prepared from cell lines and PBL samples were denaturated for 10 minutes at 70° C. Samples of lysates containing 30 µg total protein were resolved on 4-12% Bis-Tris SDS-PAGE gels (Invitrogen, Carlsbad, Calif., USA) under reducing conditions. Proteins were blotted on Protran nitrocellulose transfer membranes (Whatman, Kent, UK), blocked overnight at 4° C. with TopBlock (Fluka, Buchs, Switzerland) and incubated with 1 µg primary antibodies for 4 h at room temperature. Secondary HRP-labeled anti-mouse monoclonal antibody was applied for 1 h at room temperature. Specific binding was visualized by chemiluminescence (ECL Western Blotting Analysis System, Amersham Biosciences).

Immunofluorescence $4 \times 10^5$ cells from AML cell lines were suspended in 200 µl RPMI 1640 with 10% FCS and centrifuged on a glass slide using a Shandon CytoSpin 2 (Thermo Fisher Scientific, Waltham, Mass., USA). After the slide had dried, the cells were fixed for 10 min at room temperature using 100 µl 1% paraformaldehyde. Following one wash with 100 µl PBS, some of the cells were permeabilized for 2.5 min using 100 µl 0.1% Triton-X (Sigma-Aldrich, St. Louis, Mo., USA). Following 4 washes with PBS, the slide was incubated overnight at 4° C. in 100 µl 3% bovine serum albumin (BSA, Sigma-Aldrich). The next day, following 4 washes with PBS, the cells were incubated for 2 h at room temperature in 100 µl 0.5% BSA with 5 µg/ml specific primary or isotype control antibody. After 6 washes with PBS, a secondary fluorescein isothiocyanate (FITC)-conjugated anti mouse IgG antibody (Jackson ImmunoResearch, West Grove, Pa., USA), which was diluted 1:100 in PBS was applied for 45 min at room temperature. After four additional washes with PBS, nuclei were counterstained with 4',6-diamidino-2-phenylindole (DAPI; Boehringer Ingelheim, Ingelheim, Germany) and fluorescence was analyzed using an Axioskop 2 microscope (Zeiss, Jena, Germany).

Flow Cytometry $1 \times 10^6$ cells from cell lines or PBL samples were washed twice with 0.5% BSA. Next, the cells were resuspended in 100 µl 0.5% BSA and stained with an unconjugated anti-FMR1NB antibody or an appropriate isotype control at a 1:100 dilution for 1 h at room temperature. Following two washes with 0.5% BSA cells were stained for 30 min at room temperature with a secondary FITC-conjugated anti-mouse IgG antibody (Jackson ImmunoResearch, West Grove, Pa., USA). Following two washes with 0.5% BSA, samples were counterstained with population-specific antibodies for 15 minutes and then analyzed using a FACSCalibur cytometer and CELLQuest software (BD Biosciences).

Immunohistochemistry

Single cell layers of bone marrow biopsies from 153 newly diagnosed AML patients were spotted on microscope slides and stained by immunohistochemistry using anti-FMR1NB antibody. Images were obtained using an automated Mirax Scan system (Carl Zeiss).

Generation and Transfection of FMR1NB Expression Constructs

FMR1NB fragments were amplified from testis cDNA with the primers mentioned in Table 2, gel purified and cloned into pcDNA3.1 (Invitrogen). FMR1NB/GFP (Green fluorescence protein) fusion constructs were generated using terminal GFP fusion vectors pcDNA3.1/CT-GFP and pcDNA3.1/NT-GFP. FLAG tags were incorporated into the respective primers. Orientation and sequence identity with SEQ ID NO: 2 were confirmed by dye-terminator sequencing. HEK-293 and COS-7 cells were transfected with FMR1NB constructs using Fugene 6 transfection reagent (Roche) according to the manufacturer's instructions and analyzed by the respective readout assays 24 h after transfection.

TABLE 2

Primers for amplifying FMR1NB fragments

| Construct | | Sequence |
|---|---|---|
| FMR1NB/<br>NT-FLAG | For | AGCCATGGATGATTACAAGGATGACGACGATAAGGA<br>AAACCTGTATTTTCAGGGAGCGAAGGGGAGGAATAG<br>GAGA<br>(SEQ ID NO: 5) |
| | Rev | TGGTTTCTGTTGTCTTGAGGG<br>(SEQ ID NO: 6) |
| FMR1NB/<br>CT-FLAG | For | GGATATCGGAGCCATGTCTTCACATAGG<br>(SEQ ID NO: 7) |
| | Rev | GGCGGCCGCACTACTTATCGTCGTCATCCTTGTAAT<br>CTCCCTGAAAATACAGGTTTTCCTCGTCACCATGTT<br>CCTCAC<br>(SEQ ID NO: 8) |
| FMR1NB/<br>NT-GFP | For | CAGCGTCTCAGCGAGGCGGC<br>(SEQ ID NO: 9) |
| | Rev | GGGGACTGTCTCAGCCATGC<br>(SEQ ID NO: 10) |

TABLE 2-continued

Primers for amplifying FMR1NB fragments

| Construct | | Sequence |
|---|---|---|
| FMR1NB/<br>CT-GFP | For | GGATATCGGAGCCATGTCTTCACATAGG<br>(SEQ ID NO: 11) |
| | Rev | GGCGGCCGCATCCCTGAAAATACAGGTTTTCCTCGT<br>CACCATGTTCCTCAC<br>(SEQ ID NO: 12) |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of treating acute myeloid leukemia (AML) in a subject, comprising administering to the subject a pharmaceutical composition comprising an antibody that specifically binds FMR1NB.

2. The method of claim 1, wherein the antibody is coupled to an active compound.

3. The method of claim 2, wherein the active compound is a cytotoxic compound.

4. The method of claim 1, wherein the pharmaceutical composition is administered in an amount effective to reduce or deplete FMR1NB-positive cells from the subject.

* * * * *

SEQUENCE LISTING

<160> NUMBER OF SEQ ID NOS: 132

<210> SEQ ID NO 1
<211> LENGTH: 255
<212> TYPE: PRT
<213> ORGANISM: Homo sapiens

<400> SEQUENCE: 1

```
Met Ser Ser His Arg Arg Lys Ala Lys Gly Arg Asn Arg Arg Ser His
1               5                   10                  15

Arg Ala Met Arg Val Ala His Leu Glu Leu Ala Thr Tyr Glu Leu Ala
                20                  25                  30

Ala Thr Glu Ser Asn Pro Glu Ser Ser His Pro Gly Tyr Glu Ala Ala
            35                  40                  45

Met Ala Asp Arg Pro Gln Pro Gly Trp Arg Glu Ser Leu Lys Met Arg
        50                  55                  60

Val Ser Lys Pro Phe Gly Met Leu Met Leu Ser Ile Trp Ile Leu Leu
    65                  70                  75                  80

Phe Val Cys Tyr Tyr Leu Ser Tyr Tyr Leu Cys Ser Gly Ser Ser Tyr
                85                  90                  95

Phe Val Leu Ala Asn Gly His Ile Leu Pro Asn Ser Glu Asn Ala His
                100                 105                 110

Gly Gln Ser Leu Glu Glu Asp Ser Ala Leu Glu Ala Leu Leu Asn Phe
            115                 120                 125

Phe Phe Pro Thr Thr Cys Asn Leu Arg Glu Asn Gln Val Ala Lys Pro
        130                 135                 140

Cys Asn Glu Leu Gln Asp Leu Ser Glu Ser Glu Cys Leu Arg His Lys
    145                 150                 155                 160

Cys Cys Phe Ser Ser Ser Gly Thr Thr Ser Phe Lys Cys Phe Ala Pro
                165                 170                 175

Phe Arg Asp Val Pro Lys Gln Met Met Gln Met Phe Gly Leu Gly Ala
                180                 185                 190

Ile Ser Leu Ile Leu Val Cys Leu Pro Ile Tyr Cys Arg Ser Leu Phe
            195                 200                 205

Trp Arg Ser Glu Pro Ala Asp Asp Leu Gln Arg Gln Asp Asn Arg Val
```

```
         210                 215                 220
Val Thr Gly Leu Lys Lys Gln Arg Arg Lys Arg Lys Ser Glu
225                 230                 235                 240

Met Leu Gln Lys Ala Ala Arg Gly Arg Glu Glu His Gly Asp Glu
            245                 250                 255

<210> SEQ ID NO 2
<211> LENGTH: 768
<212> TYPE: DNA
<213> ORGANISM: Homo sapiens

<400> SEQUENCE: 2
atgtcttcac ataggaggaa agcgaagggg aggaatagga gaagtcaccg tgccatgcgt      60
gtggctcact tagagctggc aacttatgag ttggcggcaa ctgagtcgaa tcccgagagc     120
agccatcctg gatacgaggc cgccatggct gacaggcctc agccaggatg gcgggaatct     180
ctaaagatgc gggtcagcaa acccttgggg atgctcatgc tctccatttg gatcctgctg     240
ttcgtgtgct actacctgtc ctactacctg tgctccgggt cctcatattt tgtgcttgca     300
aatggacata tcctgcccaa cagtgaaaat gctcatggcc aatctctgga agaagattcc     360
gcattggaag ctttgctgaa ttttttcttt ccaacaactt gcaatctgag ggaaaatcag     420
gtggcaaagc cttgtaatga gctgcaagat cttagtgaga gtgaatgttt gagacacaaa     480
tgctgttttt catcatcggg gaccacgagc ttcaaatgtt ttgctccatt tagagatgtg     540
cctaaacaga tgatgcaaat gtttgggctt ggtgcgatca gccttatcct ggtatgtctg     600
cccatttatt gccgctctct tttctggagg agcgaaccgg ccgatgattt acaaaggcag     660
gacaacagag ttgtaacggg tttgaagaaa caagaaggga agcgaaagag gaagtctgaa     720
atgttacaga aagcagcaag aggacgtgag gaacatggtg acgagtag                  768

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
acctgtgctc cgggtcctca                                                  20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
ggctgatcgc accaagccca                                                  20

<210> SEQ ID NO 5
<211> LENGTH: 76
<212> TYPE: DNA
<213> ORGANISM: Artificial
<220> FEATURE:
<223> OTHER INFORMATION: Primer

<400> SEQUENCE: 5
agccatggat gattacaagg atgacgacga taaggaaaac ctgtattttc agggagcgaa      60
ggggaggaat aggaga                                                      76
```

```
<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
tggtttctgt tgtcttgagg g                                        21

<210> SEQ ID NO 7
<211> LENGTH: 28
<212> TYPE: DNA
<213> ORGANISM: Artificial
<220> FEATURE:
<223> OTHER INFORMATION: Primer

<400> SEQUENCE: 7
ggatatcgga gccatgtctt cacatagg                                 28

<210> SEQ ID NO 8
<211> LENGTH: 78
<212> TYPE: DNA
<213> ORGANISM: Artificial
<220> FEATURE:
<223> OTHER INFORMATION: Primer

<400> SEQUENCE: 8
ggcggccgca ctacttatcg tcgtcatcct tgtaatctcc ctgaaaatac aggttttcct    60
cgtcaccatg ttcctcac                                            78

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
cagcgtctca gcgaggcggc                                          20

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ggggactgtc tcagccatgc                                          20

<210> SEQ ID NO 11
<211> LENGTH: 28
<212> TYPE: DNA
<213> ORGANISM: Artificial
<220> FEATURE:
<223> OTHER INFORMATION: Primer

<400> SEQUENCE: 11
ggatatcgga gccatgtctt cacatagg                                 28

<210> SEQ ID NO 12
<211> LENGTH: 51
<212> TYPE: DNA
<213> ORGANISM: Artificial
<220> FEATURE:
```

<223> OTHER INFORMATION: Primer

<400> SEQUENCE: 12
ggcggccgca tccctgaaaa tacaggtttt cctcgtcacc atgttcctca c    51

<210> SEQ ID NO 13
<211> LENGTH: 9
<212> TYPE: PRT
<213> ORGANISM: Homo sapiens

<400> SEQUENCE: 13

Asn Pro Glu Ser Ser His Pro Gly Tyr
1               5

<210> SEQ ID NO 14
<211> LENGTH: 9
<212> TYPE: PRT
<213> ORGANISM: Homo sapiens

<400> SEQUENCE: 14

Leu Phe Val Cys Tyr Tyr Leu Ser Tyr
1               5

<210> SEQ ID NO 15
<211> LENGTH: 9
<212> TYPE: PRT
<213> ORGANISM: Homo sapiens

<400> SEQUENCE: 15

Ile Trp Ile Leu Leu Phe Val Cys Tyr
1               5

<210> SEQ ID NO 16
<211> LENGTH: 9
<212> TYPE: PRT
<213> ORGANISM: Homo sapiens

<400> SEQUENCE: 16

Leu Ser Glu Ser Glu Cys Leu Arg His
1               5

<210> SEQ ID NO 17
<211> LENGTH: 9
<212> TYPE: PRT
<213> ORGANISM: Homo sapiens

<400> SEQUENCE: 17

Val Ala His Leu Glu Leu Ala Thr Tyr
1               5

<210> SEQ ID NO 18
<211> LENGTH: 9
<212> TYPE: PRT
<213> ORGANISM: Homo sapiens

<400> SEQUENCE: 18

Trp Ile Leu Leu Phe Val Cys Tyr Tyr
1               5

<210> SEQ ID NO 19
<211> LENGTH: 9
<212> TYPE: PRT
<213> ORGANISM: Homo sapiens

<400> SEQUENCE: 19

```
Tyr Tyr Leu Cys Ser Gly Ser Ser Tyr
1               5

<210> SEQ ID NO 20
<211> LENGTH: 9
<212> TYPE: PRT
<213> ORGANISM: Homo sapiens

<400> SEQUENCE: 20

Leu Ile Leu Val Cys Leu Pro Ile Tyr
1               5

<210> SEQ ID NO 21
<211> LENGTH: 9
<212> TYPE: PRT
<213> ORGANISM: Homo sapiens

<400> SEQUENCE: 21

Ala Thr Glu Ser Asn Pro Glu Ser Ser
1               5

<210> SEQ ID NO 22
<211> LENGTH: 9
<212> TYPE: PRT
<213> ORGANISM: Homo sapiens

<400> SEQUENCE: 22

Phe Val Cys Tyr Tyr Leu Ser Tyr Tyr
1               5

<210> SEQ ID NO 23
<211> LENGTH: 9
<212> TYPE: PRT
<213> ORGANISM: Homo sapiens

<400> SEQUENCE: 23

Ala Ile Ser Leu Ile Leu Val Cys Leu
1               5

<210> SEQ ID NO 24
<211> LENGTH: 9
<212> TYPE: PRT
<213> ORGANISM: Homo sapiens

<400> SEQUENCE: 24

Met Leu Met Leu Ser Ile Trp Ile Leu
1               5

<210> SEQ ID NO 25
<211> LENGTH: 9
<212> TYPE: PRT
<213> ORGANISM: Homo sapiens

<400> SEQUENCE: 25

His Leu Glu Leu Ala Thr Tyr Glu Leu
1               5

<210> SEQ ID NO 26
<211> LENGTH: 9
<212> TYPE: PRT
<213> ORGANISM: Homo sapiens

<400> SEQUENCE: 26

Ile Leu Leu Phe Val Cys Tyr Tyr Leu
1               5
```

-continued

<210> SEQ ID NO 27
<211> LENGTH: 9
<212> TYPE: PRT
<213> ORGANISM: Homo sapiens

<400> SEQUENCE: 27

Ala Met Arg Val Ala His Leu Glu Leu
1               5

<210> SEQ ID NO 28
<211> LENGTH: 9
<212> TYPE: PRT
<213> ORGANISM: Homo sapiens

<400> SEQUENCE: 28

Ser Leu Ile Leu Val Cys Leu Pro Ile
1               5

<210> SEQ ID NO 29
<211> LENGTH: 9
<212> TYPE: PRT
<213> ORGANISM: Homo sapiens

<400> SEQUENCE: 29

Cys Leu Pro Ile Tyr Cys Arg Ser Leu
1               5

<210> SEQ ID NO 30
<211> LENGTH: 9
<212> TYPE: PRT
<213> ORGANISM: Homo sapiens

<400> SEQUENCE: 30

Leu Met Leu Ser Ile Trp Ile Leu Leu
1               5

<210> SEQ ID NO 31
<211> LENGTH: 9
<212> TYPE: PRT
<213> ORGANISM: Homo sapiens

<400> SEQUENCE: 31

Gly Leu Gly Ala Ile Ser Leu Ile Leu
1               5

<210> SEQ ID NO 32
<211> LENGTH: 9
<212> TYPE: PRT
<213> ORGANISM: Homo sapiens

<400> SEQUENCE: 32

Gly Met Leu Met Leu Ser Ile Trp Ile
1               5

<210> SEQ ID NO 33
<211> LENGTH: 9
<212> TYPE: PRT
<213> ORGANISM: Homo sapiens

<400> SEQUENCE: 33

Asn Leu Arg Glu Asn Gln Val Ala Lys
1               5

<210> SEQ ID NO 34
<211> LENGTH: 9

```
<212> TYPE: PRT
<213> ORGANISM: Homo sapiens

<400> SEQUENCE: 34

Lys Gln Arg Arg Lys Arg Lys Arg Lys
1               5

<210> SEQ ID NO 35
<211> LENGTH: 9
<212> TYPE: PRT
<213> ORGANISM: Homo sapiens

<400> SEQUENCE: 35

Lys Arg Lys Ser Glu Met Leu Gln Lys
1               5

<210> SEQ ID NO 36
<211> LENGTH: 9
<212> TYPE: PRT
<213> ORGANISM: Homo sapiens

<400> SEQUENCE: 36

Arg Val Ala His Leu Glu Leu Ala Thr
1               5

<210> SEQ ID NO 37
<211> LENGTH: 9
<212> TYPE: PRT
<213> ORGANISM: Homo sapiens

<400> SEQUENCE: 37

Glu Ser Leu Lys Met Arg Val Ser Lys
1               5

<210> SEQ ID NO 38
<211> LENGTH: 9
<212> TYPE: PRT
<213> ORGANISM: Homo sapiens

<400> SEQUENCE: 38

Phe Val Cys Tyr Tyr Leu Ser Tyr Tyr
1               5

<210> SEQ ID NO 39
<211> LENGTH: 9
<212> TYPE: PRT
<213> ORGANISM: Homo sapiens

<400> SEQUENCE: 39

Tyr Leu Cys Ser Gly Ser Ser Tyr Phe
1               5

<210> SEQ ID NO 40
<211> LENGTH: 9
<212> TYPE: PRT
<213> ORGANISM: Homo sapiens

<400> SEQUENCE: 40

Ala Leu Glu Ala Leu Leu Asn Phe Phe
1               5

<210> SEQ ID NO 41
<211> LENGTH: 9
<212> TYPE: PRT
<213> ORGANISM: Homo sapiens
```

```
<400> SEQUENCE: 41

Ser Leu Ile Leu Val Cys Leu Pro Ile
1               5

<210> SEQ ID NO 42
<211> LENGTH: 9
<212> TYPE: PRT
<213> ORGANISM: Homo sapiens

<400> SEQUENCE: 42

Val Val Thr Gly Leu Lys Lys Gln Arg
1               5

<210> SEQ ID NO 43
<211> LENGTH: 9
<212> TYPE: PRT
<213> ORGANISM: Homo sapiens

<400> SEQUENCE: 43

Tyr Phe Val Leu Ala Asn Gly His Ile
1               5

<210> SEQ ID NO 44
<211> LENGTH: 9
<212> TYPE: PRT
<213> ORGANISM: Homo sapiens

<400> SEQUENCE: 44

Phe Phe Phe Pro Thr Thr Cys Asn Leu
1               5

<210> SEQ ID NO 45
<211> LENGTH: 9
<212> TYPE: PRT
<213> ORGANISM: Homo sapiens

<400> SEQUENCE: 45

Pro Phe Gly Met Leu Met Leu Ser Ile
1               5

<210> SEQ ID NO 46
<211> LENGTH: 9
<212> TYPE: PRT
<213> ORGANISM: Homo sapiens

<400> SEQUENCE: 46

Met Phe Gly Leu Gly Ala Ile Ser Leu
1               5

<210> SEQ ID NO 47
<211> LENGTH: 9
<212> TYPE: PRT
<213> ORGANISM: Homo sapiens

<400> SEQUENCE: 47

Leu Met Leu Ser Ile Trp Ile Leu Leu
1               5

<210> SEQ ID NO 48
<211> LENGTH: 9
<212> TYPE: PRT
<213> ORGANISM: Homo sapiens

<400> SEQUENCE: 48

Phe Gly Leu Gly Ala Ile Ser Leu Ile
```

<210> SEQ ID NO 49
<211> LENGTH: 9
<212> TYPE: PRT
<213> ORGANISM: Homo sapiens

<400> SEQUENCE: 49

Gln Ser Leu Glu Glu Asp Ser Ala Leu
1               5

<210> SEQ ID NO 50
<211> LENGTH: 9
<212> TYPE: PRT
<213> ORGANISM: Homo sapiens

<400> SEQUENCE: 50

Ser Ala Leu Glu Ala Leu Leu Asn Phe
1               5

<210> SEQ ID NO 51
<211> LENGTH: 9
<212> TYPE: PRT
<213> ORGANISM: Homo sapiens

<400> SEQUENCE: 51

Leu Pro Ile Tyr Cys Arg Ser Leu Phe
1               5

<210> SEQ ID NO 52
<211> LENGTH: 9
<212> TYPE: PRT
<213> ORGANISM: Homo sapiens

<400> SEQUENCE: 52

His Arg Ala Met Arg Val Ala His Leu
1               5

<210> SEQ ID NO 53
<211> LENGTH: 9
<212> TYPE: PRT
<213> ORGANISM: Homo sapiens

<400> SEQUENCE: 53

Lys Pro Cys Asn Glu Leu Gln Asp Leu
1               5

<210> SEQ ID NO 54
<211> LENGTH: 9
<212> TYPE: PRT
<213> ORGANISM: Homo sapiens

<400> SEQUENCE: 54

His Pro Gly Tyr Glu Ala Ala Met Ala
1               5

<210> SEQ ID NO 55
<211> LENGTH: 9
<212> TYPE: PRT
<213> ORGANISM: Homo sapiens

<400> SEQUENCE: 55

Arg Val Ser Lys Pro Phe Gly Met Leu
1               5

```
<210> SEQ ID NO 56
<211> LENGTH: 9
<212> TYPE: PRT
<213> ORGANISM: Homo sapiens

<400> SEQUENCE: 56

Leu Pro Ile Tyr Cys Arg Ser Leu Phe
1               5

<210> SEQ ID NO 57
<211> LENGTH: 9
<212> TYPE: PRT
<213> ORGANISM: Homo sapiens

<400> SEQUENCE: 57

Ala Met Arg Val Ala His Leu Glu Leu
1               5

<210> SEQ ID NO 58
<211> LENGTH: 9
<212> TYPE: PRT
<213> ORGANISM: Homo sapiens

<400> SEQUENCE: 58

Val Pro Lys Gln Met Met Gln Met Phe
1               5

<210> SEQ ID NO 59
<211> LENGTH: 9
<212> TYPE: PRT
<213> ORGANISM: Homo sapiens

<400> SEQUENCE: 59

Ala Ile Ser Leu Ile Leu Val Cys Leu
1               5

<210> SEQ ID NO 60
<211> LENGTH: 9
<212> TYPE: PRT
<213> ORGANISM: Homo sapiens

<400> SEQUENCE: 60

Glu Asp Ser Ala Leu Glu Ala Leu Leu
1               5

<210> SEQ ID NO 61
<211> LENGTH: 9
<212> TYPE: PRT
<213> ORGANISM: Homo sapiens

<400> SEQUENCE: 61

Gln Val Ala Lys Pro Cys Asn Glu Leu
1               5

<210> SEQ ID NO 62
<211> LENGTH: 9
<212> TYPE: PRT
<213> ORGANISM: Homo sapiens

<400> SEQUENCE: 62

Trp Arg Ser Glu Pro Ala Asp Asp Leu
1               5

<210> SEQ ID NO 63
<211> LENGTH: 9
<212> TYPE: PRT
```

<213> ORGANISM: Homo sapiens

<400> SEQUENCE: 63

Lys Arg Lys Arg Lys Ser Glu Met Leu
1               5

<210> SEQ ID NO 64
<211> LENGTH: 9
<212> TYPE: PRT
<213> ORGANISM: Homo sapiens

<400> SEQUENCE: 64

Ser Leu Lys Met Arg Val Ser Lys Pro
1               5

<210> SEQ ID NO 65
<211> LENGTH: 9
<212> TYPE: PRT
<213> ORGANISM: Homo sapiens

<400> SEQUENCE: 65

Lys Ala Lys Gly Arg Asn Arg Arg Ser
1               5

<210> SEQ ID NO 66
<211> LENGTH: 9
<212> TYPE: PRT
<213> ORGANISM: Homo sapiens

<400> SEQUENCE: 66

Val Pro Lys Gln Met Met Gln Met Phe
1               5

<210> SEQ ID NO 67
<211> LENGTH: 9
<212> TYPE: PRT
<213> ORGANISM: Homo sapiens

<400> SEQUENCE: 67

Cys Leu Arg His Lys Cys Cys Phe Ser
1               5

<210> SEQ ID NO 68
<211> LENGTH: 9
<212> TYPE: PRT
<213> ORGANISM: Homo sapiens

<400> SEQUENCE: 68

Arg Arg Lys Arg Lys Arg Lys Ser Glu
1               5

<210> SEQ ID NO 69
<211> LENGTH: 9
<212> TYPE: PRT
<213> ORGANISM: Homo sapiens

<400> SEQUENCE: 69

Arg Arg Lys Ala Lys Gly Arg Asn Arg
1               5

<210> SEQ ID NO 70
<211> LENGTH: 9
<212> TYPE: PRT
<213> ORGANISM: Homo sapiens

<400> SEQUENCE: 70

His Arg Ala Met Arg Val Ala His Leu
1               5

<210> SEQ ID NO 71
<211> LENGTH: 9
<212> TYPE: PRT
<213> ORGANISM: Homo sapiens

<400> SEQUENCE: 71

Ser His Arg Arg Lys Ala Lys Gly Arg
1               5

<210> SEQ ID NO 72
<211> LENGTH: 9
<212> TYPE: PRT
<213> ORGANISM: Homo sapiens

<400> SEQUENCE: 72

His Leu Glu Leu Ala Thr Tyr Glu Leu
1               5

<210> SEQ ID NO 73
<211> LENGTH: 9
<212> TYPE: PRT
<213> ORGANISM: Homo sapiens

<400> SEQUENCE: 73

Met Leu Ser Ile Trp Ile Leu Leu Phe
1               5

<210> SEQ ID NO 74
<211> LENGTH: 9
<212> TYPE: PRT
<213> ORGANISM: Homo sapiens

<400> SEQUENCE: 74

Tyr Leu Cys Ser Gly Ser Ser Tyr Phe
1               5

<210> SEQ ID NO 75
<211> LENGTH: 9
<212> TYPE: PRT
<213> ORGANISM: Homo sapiens

<400> SEQUENCE: 75

Phe Val Cys Tyr Tyr Leu Ser Tyr Tyr
1               5

<210> SEQ ID NO 76
<211> LENGTH: 9
<212> TYPE: PRT
<213> ORGANISM: Homo sapiens

<400> SEQUENCE: 76

Ala Leu Glu Ala Leu Leu Asn Phe Phe
1               5

<210> SEQ ID NO 77
<211> LENGTH: 9
<212> TYPE: PRT
<213> ORGANISM: Homo sapiens

<400> SEQUENCE: 77

Trp Ile Leu Leu Phe Val Cys Tyr Tyr
1               5

```
<210> SEQ ID NO 78
<211> LENGTH: 9
<212> TYPE: PRT
<213> ORGANISM: Homo sapiens

<400> SEQUENCE: 78

Leu Ile Leu Val Cys Leu Pro Ile Tyr
1               5

<210> SEQ ID NO 79
<211> LENGTH: 9
<212> TYPE: PRT
<213> ORGANISM: Homo sapiens

<400> SEQUENCE: 79

Ser Leu Lys Met Arg Val Ser Lys Pro
1               5

<210> SEQ ID NO 80
<211> LENGTH: 9
<212> TYPE: PRT
<213> ORGANISM: Homo sapiens

<400> SEQUENCE: 80

Asn Leu Arg Glu Asn Gln Val Ala Lys
1               5

<210> SEQ ID NO 81
<211> LENGTH: 9
<212> TYPE: PRT
<213> ORGANISM: Homo sapiens

<400> SEQUENCE: 81

Ser Leu Ile Leu Val Cys Leu Pro Ile
1               5

<210> SEQ ID NO 82
<211> LENGTH: 9
<212> TYPE: PRT
<213> ORGANISM: Homo sapiens

<400> SEQUENCE: 82

Val Ala His Leu Glu Leu Ala Thr Tyr
1               5

<210> SEQ ID NO 83
<211> LENGTH: 9
<212> TYPE: PRT
<213> ORGANISM: Homo sapiens

<400> SEQUENCE: 83

Glu Glu Asp Ser Ala Leu Glu Ala Leu
1               5

<210> SEQ ID NO 84
<211> LENGTH: 9
<212> TYPE: PRT
<213> ORGANISM: Homo sapiens

<400> SEQUENCE: 84

Ser Glu Asn Ala His Gly Gln Ser Leu
1               5

<210> SEQ ID NO 85
```

```
<211> LENGTH: 9
<212> TYPE: PRT
<213> ORGANISM: Homo sapiens

<400> SEQUENCE: 85

Leu Glu Ala Leu Leu Asn Phe Phe Phe
1               5

<210> SEQ ID NO 86
<211> LENGTH: 9
<212> TYPE: PRT
<213> ORGANISM: Homo sapiens

<400> SEQUENCE: 86

Ala Ile Ser Leu Ile Leu Val Cys Leu
1               5

<210> SEQ ID NO 87
<211> LENGTH: 9
<212> TYPE: PRT
<213> ORGANISM: Homo sapiens

<400> SEQUENCE: 87

Met Leu Ser Ile Trp Ile Leu Leu Phe
1               5

<210> SEQ ID NO 88
<211> LENGTH: 9
<212> TYPE: PRT
<213> ORGANISM: Homo sapiens

<400> SEQUENCE: 88

Ile Trp Ile Leu Leu Phe Val Cys Tyr
1               5

<210> SEQ ID NO 89
<211> LENGTH: 9
<212> TYPE: PRT
<213> ORGANISM: Homo sapiens

<400> SEQUENCE: 89

Phe Phe Phe Pro Thr Thr Cys Asn Leu
1               5

<210> SEQ ID NO 90
<211> LENGTH: 9
<212> TYPE: PRT
<213> ORGANISM: Homo sapiens

<400> SEQUENCE: 90

Met Leu Met Leu Ser Ile Trp Ile Leu
1               5

<210> SEQ ID NO 91
<211> LENGTH: 9
<212> TYPE: PRT
<213> ORGANISM: Homo sapiens

<400> SEQUENCE: 91

Ala Leu Glu Ala Leu Leu Asn Phe Phe
1               5

<210> SEQ ID NO 92
<211> LENGTH: 9
<212> TYPE: PRT
<213> ORGANISM: Homo sapiens
```

```
<400> SEQUENCE: 92

Ser Glu Cys Leu Arg His Lys Cys Cys
1               5

<210> SEQ ID NO 93
<211> LENGTH: 15
<212> TYPE: PRT
<213> ORGANISM: Homo sapiens

<400> SEQUENCE: 93

Met Met Gln Met Phe Gly Leu Gly Ala Ile Ser Leu Ile Leu Val
1               5                   10                  15

<210> SEQ ID NO 94
<211> LENGTH: 15
<212> TYPE: PRT
<213> ORGANISM: Homo sapiens

<400> SEQUENCE: 94

Pro Lys Gln Met Met Gln Met Phe Gly Leu Gly Ala Ile Ser Leu
1               5                   10                  15

<210> SEQ ID NO 95
<211> LENGTH: 15
<212> TYPE: PRT
<213> ORGANISM: Homo sapiens

<400> SEQUENCE: 95

Ser Ser Tyr Phe Val Leu Ala Asn Gly His Ile Leu Pro Asn Ser
1               5                   10                  15

<210> SEQ ID NO 96
<211> LENGTH: 15
<212> TYPE: PRT
<213> ORGANISM: Homo sapiens

<400> SEQUENCE: 96

Ser Leu Phe Trp Arg Ser Glu Pro Ala Asp Asp Leu Gln Arg Gln
1               5                   10                  15

<210> SEQ ID NO 97
<211> LENGTH: 15
<212> TYPE: PRT
<213> ORGANISM: Homo sapiens

<400> SEQUENCE: 97

His Pro Gly Tyr Glu Ala Ala Met Ala Asp Arg Pro Gln Pro Gly
1               5                   10                  15

<210> SEQ ID NO 98
<211> LENGTH: 15
<212> TYPE: PRT
<213> ORGANISM: Homo sapiens

<400> SEQUENCE: 98

Ser Leu Lys Met Arg Val Ser Lys Pro Phe Gly Met Leu Met Leu
1               5                   10                  15

<210> SEQ ID NO 99
<211> LENGTH: 15
<212> TYPE: PRT
<213> ORGANISM: Homo sapiens

<400> SEQUENCE: 99
```

```
Lys Met Arg Val Ser Lys Pro Phe Gly Met Leu Met Leu Ser Ile
1               5                   10                  15
```

<210> SEQ ID NO 100
<211> LENGTH: 15
<212> TYPE: PRT
<213> ORGANISM: Homo sapiens

<400> SEQUENCE: 100

```
Gly Ser Ser Tyr Phe Val Leu Ala Asn Gly His Ile Leu Pro Asn
1               5                   10                  15
```

<210> SEQ ID NO 101
<211> LENGTH: 15
<212> TYPE: PRT
<213> ORGANISM: Homo sapiens

<400> SEQUENCE: 101

```
Lys Cys Cys Phe Ser Ser Ser Gly Thr Thr Ser Phe Lys Cys Phe
1               5                   10                  15
```

<210> SEQ ID NO 102
<211> LENGTH: 15
<212> TYPE: PRT
<213> ORGANISM: Homo sapiens

<400> SEQUENCE: 102

```
Phe Ala Pro Phe Arg Asp Val Pro Lys Gln Met Met Gln Met Phe
1               5                   10                  15
```

<210> SEQ ID NO 103
<211> LENGTH: 15
<212> TYPE: PRT
<213> ORGANISM: Homo sapiens

<400> SEQUENCE: 103

```
Asp Ser Ala Leu Glu Ala Leu Leu Asn Phe Phe Phe Pro Thr Thr
1               5                   10                  15
```

<210> SEQ ID NO 104
<211> LENGTH: 15
<212> TYPE: PRT
<213> ORGANISM: Homo sapiens

<400> SEQUENCE: 104

```
Leu Val Cys Leu Pro Ile Tyr Cys Arg Ser Leu Phe Trp Arg Ser
1               5                   10                  15
```

<210> SEQ ID NO 105
<211> LENGTH: 15
<212> TYPE: PRT
<213> ORGANISM: Homo sapiens

<400> SEQUENCE: 105

```
Gly Met Leu Met Leu Ser Ile Trp Ile Leu Leu Phe Val Cys Tyr
1               5                   10                  15
```

<210> SEQ ID NO 106
<211> LENGTH: 15
<212> TYPE: PRT
<213> ORGANISM: Homo sapiens

<400> SEQUENCE: 106

```
Gly Gln Ser Leu Glu Glu Asp Ser Ala Leu Glu Ala Leu Leu Asn
1               5                   10                  15
```

```
<210> SEQ ID NO 107
<211> LENGTH: 15
<212> TYPE: PRT
<213> ORGANISM: Homo sapiens

<400> SEQUENCE: 107

Pro Phe Gly Met Leu Met Leu Ser Ile Trp Ile Leu Leu Phe Val
1               5                   10                  15

<210> SEQ ID NO 108
<211> LENGTH: 15
<212> TYPE: PRT
<213> ORGANISM: Homo sapiens

<400> SEQUENCE: 108

Asn Gly His Ile Leu Pro Asn Ser Glu Asn Ala His Gly Gln Ser
1               5                   10                  15

<210> SEQ ID NO 109
<211> LENGTH: 15
<212> TYPE: PRT
<213> ORGANISM: Homo sapiens

<400> SEQUENCE: 109

Ser Ile Trp Ile Leu Leu Phe Val Cys Tyr Tyr Leu Ser Tyr Tyr
1               5                   10                  15

<210> SEQ ID NO 110
<211> LENGTH: 15
<212> TYPE: PRT
<213> ORGANISM: Homo sapiens

<400> SEQUENCE: 110

Ala Met Arg Val Ala His Leu Glu Leu Ala Thr Tyr Glu Leu Ala
1               5                   10                  15

<210> SEQ ID NO 111
<211> LENGTH: 15
<212> TYPE: PRT
<213> ORGANISM: Homo sapiens

<400> SEQUENCE: 111

Arg Glu Ser Leu Lys Met Arg Val Ser Lys Pro Phe Gly Met Leu
1               5                   10                  15

<210> SEQ ID NO 112
<211> LENGTH: 15
<212> TYPE: PRT
<213> ORGANISM: Homo sapiens

<400> SEQUENCE: 112

Phe Gly Met Leu Met Leu Ser Ile Trp Ile Leu Leu Phe Val Cys
1               5                   10                  15

<210> SEQ ID NO 113
<211> LENGTH: 15
<212> TYPE: PRT
<213> ORGANISM: Homo sapiens

<400> SEQUENCE: 113

Leu Ala Thr Tyr Glu Leu Ala Ala Thr Glu Ser Asn Pro Glu Ser
1               5                   10                  15

<210> SEQ ID NO 114
<211> LENGTH: 15
```

```
<212> TYPE: PRT
<213> ORGANISM: Homo sapiens

<400> SEQUENCE: 114

Gly Ser Ser Tyr Phe Val Leu Ala Asn Gly His Ile Leu Pro Asn
1               5                   10                  15

<210> SEQ ID NO 115
<211> LENGTH: 15
<212> TYPE: PRT
<213> ORGANISM: Homo sapiens

<400> SEQUENCE: 115

Ser Ser Tyr Phe Val Leu Ala Asn Gly His Ile Leu Pro Asn Ser
1               5                   10                  15

<210> SEQ ID NO 116
<211> LENGTH: 15
<212> TYPE: PRT
<213> ORGANISM: Homo sapiens

<400> SEQUENCE: 116

Leu Leu Asn Phe Phe Phe Pro Thr Thr Cys Asn Leu Arg Glu Asn
1               5                   10                  15

<210> SEQ ID NO 117
<211> LENGTH: 15
<212> TYPE: PRT
<213> ORGANISM: Homo sapiens

<400> SEQUENCE: 117

Phe Lys Cys Phe Ala Pro Phe Arg Asp Val Pro Lys Gln Met Met
1               5                   10                  15

<210> SEQ ID NO 118
<211> LENGTH: 15
<212> TYPE: PRT
<213> ORGANISM: Homo sapiens

<400> SEQUENCE: 118

Phe Ala Pro Phe Arg Asp Val Pro Lys Gln Met Met Gln Met Phe
1               5                   10                  15

<210> SEQ ID NO 119
<211> LENGTH: 15
<212> TYPE: PRT
<213> ORGANISM: Homo sapiens

<400> SEQUENCE: 119

Ser Leu Phe Trp Arg Ser Glu Pro Ala Asp Asp Leu Gln Arg Gln
1               5                   10                  15

<210> SEQ ID NO 120
<211> LENGTH: 15
<212> TYPE: PRT
<213> ORGANISM: Homo sapiens

<400> SEQUENCE: 120

His Arg Ala Met Arg Val Ala His Leu Glu Leu Ala Thr Tyr Glu
1               5                   10                  15

<210> SEQ ID NO 121
<211> LENGTH: 15
<212> TYPE: PRT
<213> ORGANISM: Homo sapiens
```

```
<400> SEQUENCE: 121

Val Ala His Leu Glu Leu Ala Thr Tyr Glu Leu Ala Ala Thr Glu
1               5                   10                  15

<210> SEQ ID NO 122
<211> LENGTH: 15
<212> TYPE: PRT
<213> ORGANISM: Homo sapiens

<400> SEQUENCE: 122

Pro Phe Gly Met Leu Met Leu Ser Ile Trp Ile Leu Leu Phe Val
1               5                   10                  15

<210> SEQ ID NO 123
<211> LENGTH: 15
<212> TYPE: PRT
<213> ORGANISM: Homo sapiens

<400> SEQUENCE: 123

Leu Ser Tyr Tyr Leu Cys Ser Gly Ser Ser Tyr Phe Val Leu Ala
1               5                   10                  15

<210> SEQ ID NO 124
<211> LENGTH: 15
<212> TYPE: PRT
<213> ORGANISM: Homo sapiens

<400> SEQUENCE: 124

Lys Cys Cys Phe Ser Ser Ser Gly Thr Thr Ser Phe Lys Cys Phe
1               5                   10                  15

<210> SEQ ID NO 125
<211> LENGTH: 15
<212> TYPE: PRT
<213> ORGANISM: Homo sapiens

<400> SEQUENCE: 125

Leu Leu Asn Phe Phe Phe Pro Thr Thr Cys Asn Leu Arg Glu Asn
1               5                   10                  15

<210> SEQ ID NO 126
<211> LENGTH: 15
<212> TYPE: PRT
<213> ORGANISM: Homo sapiens

<400> SEQUENCE: 126

Leu Ala Thr Tyr Glu Leu Ala Ala Thr Glu Ser Asn Pro Glu Ser
1               5                   10                  15

<210> SEQ ID NO 127
<211> LENGTH: 15
<212> TYPE: PRT
<213> ORGANISM: Homo sapiens

<400> SEQUENCE: 127

Thr Tyr Glu Leu Ala Ala Thr Glu Ser Asn Pro Glu Ser Ser His
1               5                   10                  15

<210> SEQ ID NO 128
<211> LENGTH: 15
<212> TYPE: PRT
<213> ORGANISM: Homo sapiens

<400> SEQUENCE: 128

Gln Pro Gly Trp Arg Glu Ser Leu Lys Met Arg Val Ser Lys Pro
```

```
1               5                   10                  15
```

<210> SEQ ID NO 129
<211> LENGTH: 15
<212> TYPE: PRT
<213> ORGANISM: Homo sapiens

<400> SEQUENCE: 129

```
Leu Leu Phe Val Cys Tyr Tyr Leu Ser Tyr Tyr Leu Cys Ser Gly
1               5                   10                  15
```

<210> SEQ ID NO 130
<211> LENGTH: 15
<212> TYPE: PRT
<213> ORGANISM: Homo sapiens

<400> SEQUENCE: 130

```
Ser Tyr Tyr Leu Cys Ser Gly Ser Ser Tyr Phe Val Leu Ala Asn
1               5                   10                  15
```

<210> SEQ ID NO 131
<211> LENGTH: 15
<212> TYPE: PRT
<213> ORGANISM: Homo sapiens

<400> SEQUENCE: 131

```
Gly Ser Ser Tyr Phe Val Leu Ala Asn Gly His Ile Leu Pro Asn
1               5                   10                  15
```

<210> SEQ ID NO 132
<211> LENGTH: 15
<212> TYPE: PRT
<213> ORGANISM: Homo sapiens

<400> SEQUENCE: 132

```
Ser Ser Tyr Phe Val Leu Ala Asn Gly His Ile Leu Pro Asn Ser
1               5                   10                  15
```